US007575751B2

(12) United States Patent
Vale et al.

(10) Patent No.: US 7,575,751 B2
(45) Date of Patent: Aug. 18, 2009

(54) ACTIVIN-A MUTANTS

(75) Inventors: Wylie Vale, La Jolla, CA (US); Craig Harrison, Nunawading (AU); Peter Gray, Encinitas, CA (US); Wolfgang Fischer, Encinitas, CA (US); Senyon Choe, Solana Beach, CA (US)

(73) Assignee: Research Development Foundation, Carson City, NV (US)

( * ) Notice: Subject to any disclaimer, the term of this patent is extended or adjusted under 35 U.S.C. 154(b) by 43 days.

(21) Appl. No.: 11/115,877

(22) Filed: Apr. 27, 2005

(65) Prior Publication Data
US 2006/0008846 A1    Jan. 12, 2006

Related U.S. Application Data

(60) Provisional application No. 60/565,594, filed on Apr. 27, 2004.

(51) Int. Cl.
*A61K 39/00* (2006.01)
*C07K 14/00* (2006.01)

(52) U.S. Cl. .................................. 424/198.1; 530/350

(58) Field of Classification Search ........................ None
See application file for complete search history.

(56) References Cited

U.S. PATENT DOCUMENTS

| 4,886,747 A | 12/1989 | Derynck et al. |
| 5,011,691 A | 4/1991 | Oppermann et al. |
| 5,013,649 A | 5/1991 | Wang et al. |
| 5,106,748 A | 4/1992 | Wozney et al. |
| 5,108,922 A | 4/1992 | Wang et al. |
| 5,116,738 A | 5/1992 | Wang et al. |
| 5,141,905 A | 8/1992 | Rosen et al. |
| 5,187,076 A | 2/1993 | Wozney et al. |
| 5,284,763 A | 2/1994 | Derynk et al. |
| 5,652,337 A | 7/1997 | Oppermann et al. |
| 5,658,882 A | 8/1997 | Celeste et al. |
| 5,965,403 A | 10/1999 | Celeste et al. |
| 6,027,919 A | 2/2000 | Celeste et al. |

FOREIGN PATENT DOCUMENTS

| EP | 0222491 | 5/1987 |
| EP | 0376785 | 7/1990 |
| WO | WO-91/05802 | 5/1991 |
| WO | WO-91/18098 | 11/1991 |
| WO | WO-92/00382 | 1/1992 |
| WO | WO-93/00432 | 1/1993 |
| WO | WO-93/16099 | 8/1993 |
| WO | WO-94/01557 | 1/1994 |
| WO | WO-94/15949 | 7/1994 |
| WO | WO-94/21681 | 9/1994 |
| WO | WO-94/26892 | 11/1994 |
| WO | WO-94/26893 | 11/1994 |
| WO | WO-95/01801 | 1/1995 |
| WO | WO-95/01802 | 1/1995 |
| WO | WO-95/04819 | 2/1995 |
| WO | WO-95/10539 | 4/1995 |
| WO | WO-95/10635 | 4/1995 |
| WO | WO-95/16035 | 4/1995 |
| WO | WO-96/01316 | 1/1996 |
| WO | WO-96/01845 | 1/1996 |
| WO | WO-96/02559 | 2/1996 |
| WO | WO-96/14335 | 5/1996 |
| WO | WO-96/36710 | 11/1996 |
| WO | WO-97/00958 | 1/1997 |
| WO | WO-97/36926 | 10/1997 |
| WO | WO-98/22492 | 5/1998 |
| WO | WO-99/06445 | 2/1999 |

OTHER PUBLICATIONS

Husken-Hindi P., et al. Monomeric activin A retains high receptor binding affinity but exhibits low biological activity. J. Biol. Chem. 1994, vol. 269, pp. 19380-19384.*
Lin, SJ. et al. The structural basis of TGF-b, bone morphogenetic protein, and activin ligand binding. Reproduction. 2006. vol. 132, p. 179-190.*
Lopez-Ilasaca M, et al. The angiotensis II type I receptor-associated protein, ATRAP, is a transmembrane protein and a modulator of angiotensis II signaling. Molecular Biology, 2003. vol. 14, p. 5038-5050.*
Bergholdt R, et al. Characterization of new polymorphisms in the 5' UTR of the human interleukin-1 receptor type I (IL1R1) gene: linkage to type I diabetes and correlation to IL-1R1 plasma level. Genes and Immunity. 2001. vol. 1, p. 495-500.*
Grant, ES, et al. The insulin-like growth factor type I receptor stimulates growth and suppresses apoptosis in prostatic stromal cells. Journal of Clinical Endocrinology and Metabolism. 1998. vol. 83, p. 3252-3257.*
Arora et al., "The *screw* gene encodes a ubiquitously expressed member of the TGF-β family required for specification of dorsal call fates in the *Drosophila* embryo," *Genes Dev.*, 8(21): 2588-2601, 1994.
Baloh et al., "Artemin, a Novel Member of the GDNF Ligand Family, Supports Peripheral and Central Neurons and Signals through the GFRα3-RET Receptor Complex," *Neuron*, 21(6): 1291-1302, 1998.
Basler et al., "Control of Cell Pattern in the Neural Tube: Regulation of Cell Differentiation by *dorsalin*-1, a Novel TGFβ Family Member," *Cell*, 73(4): 687-702, 1993.
Bootcov et al., "MIC-1, a novel microphage inhibitory cytokine, is a divergent member of the TGF-β superfamily," *Proc. Natl. Acad. Sci. USA*, 94(21): 11514-11519, 1997.
Cate et al., "Isolation of the Bovine and Human Genes for Müllerian Inhibiting Substance and Expression of the Human Gene in Animal Cells," *Cell*, 45: 685-698, 1986.

(Continued)

*Primary Examiner*—Robert Landsman
*Assistant Examiner*—Bruce D Hissong
(74) *Attorney, Agent, or Firm*—Fulbright & Jaworski LLP

(57) ABSTRACT

Members of the TGF-β superfamily control many physiologic and pathophysiologic processes in multiple tissues and signal via type II and type I receptor serine kinases. Type II activin receptors are promiscuous and known to bind 12 TGF-β ligands including activins, myostatin, BMPs and nodal. Methods are described for the screening and identification of antagonist for TGF-β superfamily members, in particular activin-A antagonist.

8 Claims, 12 Drawing Sheets

OTHER PUBLICATIONS

Genback accession No. NM_002192.

Kotzbauer et al., "Neurturin, a relative of glial-cell-line-derived neurotrophic factor," *Nature*, 384(6608): 467-470, 1996.

Lin et al., "GDNF: A Glial Cell Line-Derived Neurotrophic Factor for Midbrain Dopaminergic Neurons," *Science*, 260(5111): 1130-1132, 1993.

Lyons et al., "*Vgr-1*, a mammalian gene related to *Xenopus Vg-1*, is a member of the transforming growth factor β gene superfamily," *Proc. Natl. Acad. Sci. USA*, 86(12): 4554-4558, 1989.

Milbrandt et al., "Persephin, a Novel Neurotrophic Factor Related to GDNF and Neurturin," *Neuron*, 20: 245-253, 1998.

Moos et al., "Anti-Dorsalizing Morphogenetic Protein is a novel TGF-β homolog expressed in the Spemann organizer," *Development*, 121(12): 4293-4301, 1995.

Oda et al., "Molecular Cloning and Functional Analysis of a New Activin β Subunit: A Dorsal Mesoderm-Inducing Activity in Xenopus," *Biochem. Biophys. Res. Commun.*, 210(2): 581-588, 1995.

Padgett et al., "A transcript from a Drosophila pattern gene predicts a protein homologous to the transforming growth factor-β family," *Nature*, 325(6099): 81-4, 1987.

Stenzel et al., "The Univin Gene Encodes a Member of the Transforming Growth Factor-β Superfamily with Restricted Expression in the Sea Urchin Embryo," *Dev. Biol.*, 166(1): 149-158, 1994.

Weeks and Mellon, "A Maternal mRNA Localized to the Vegetal Hemisphere in Xenopus Eggs Codes for a Growth Factor Related to TGF-β," *Cell*, 51(5): 861-867, 1987.

Zhou et al., "Nodal is a novel TGF-β-like gene expressed in the mouse node during gastrulation," *Nature*, 361(6412): 543-547, 1993.

Fischer et al., "Residues in the C-terminal region of activin A determine specificity for follistatin and type II receptor binding," *Journal of Endocrinology*, 176(1):61-68, 2003.

Harrison et al., "An activin mutant with disrupted ALK4 binding blocks signaling via type II receptors," *J. of Biological Chemistry.*, 279(27):28036-28044, 2004.

Harrison et al., "Identification of a functional binding site for activin on the type I receptor ALK4," *Journal of Biological Chemistry*, 278(23):21129-21135, 2003.

Massague, "TGF-beta signal transduction," *Annual Review of Biochemistry*, 67:753-791, 1998.

* cited by examiner

FIG. 2

Y-axis: % 125-activin-A bound

A

Y-axis: FSH released (ng/ml)

B

Y-axis: FSH released (ng/ml)

ACTIVIN-A MUTANTS

This application claims priority to U.S. Provisional Application Ser. No. 60/565,594, filed Apr. 27, 2004, which is incorporated herein by reference in its entirety.

This invention was made with government support under grant numbers HD-13527 and HD042362-03 awarded by the National Institutes of Health and under a CJ Martin Fellowship from the Medical Research Council, Australia. The government has certain rights in the invention.

BACKGROUND OF THE INVENTION

I. Field of the Invention

The present invention relates generally to the fields of cellular and molecular biology. More specifically, the present invention relates to antagonism of TGF-β receptors by variants of the TGF-β superfamily of ligands and uses thereof.

II. Description of Related Art

The transforming growth factor β (TGF-β) superfamily comprises over 30 secreted ligands in humans that control cell proliferation, cell death, metabolism, homeostasis, differentiation, tissue development, immune responses, angiogenesis, wound repair, endocrine function and many other physiologic processes. Members of this superfamily include TGF-β, activin, bone morphogenetic protein (BMP), Growth and Differentiation Factor (GDF) and nodal-related families. Disruption or dysregulated activity of TGF-β superfamily members is associated with multiple pathological states resulting from processes including aberrant cellular differentiation, proliferation and/or metabolism.

TGF-β superfamily members share a distinct structural framework known as the cystine knot scaffold. Activins adopt this prototypical disulfide-linked dimeric structure and consist of two β chains. Although there are several activin β subunit genes and an extensive array of possible β-β dimers, only βA-βA (activin-A), βA-βB (activin-AB) and βB-βB (activin-B) have been isolated as dimeric proteins and shown to be biologically active. Similar to other TGF-β superfamily members, activins derive from large precursor proteins consisting of an N-terminal prodomain and a C-terminal β subunit domain that is released following proteolysis. In the case of activins the prodomain aids in proper folding, disulfide bond formation and dimerization of the β subunit domains after which the mature active β subunit dimers are cleaved and released. In the case of other TGF-β superfamily members, such as the TGF-β isoforms and myostatin (GDF8), however, the prodomain remains bound to the mature ligand to inhibit its activity.

Signaling via Receptor Serine Kinases—Activins and other TGF-β superfamily members exert their biological effects by interacting with two types of cell surface transmembrane receptors (type I and type II receptors) with intrinsic serine/threonine kinase activities, called receptor serine kinases (RSKs). The type II activin receptor (ActRII) was the first RSK to be cloned and led to the cloning of four additional type II RSKs and seven type I RSKs in human. The type I RSKs are referred to as ALK1 to ALK7, for Activin receptor-Like Kinases. The receptor activation mechanism for all TGF-β ligands involves both receptor types. This was first established for TGF-β that was shown to bind its type II receptor (TβRII) leading to the recruitment, phosphorylation and activation of its type I receptor (ALK5) followed by activation of intracellular signaling. A similar mechanism of ligand-mediated receptor assembly and type I receptor phosphorylation was demonstrated for activin-A, although activin-A binds ActRII or ActRIIB followed by recruitment, phosphorylation and activation of its type I receptor ALK4. Considerable promiscuity exists in the interactions between TGF-β ligands and receptors since there are over 30 ligands in human signaling via only five type II receptors and seven type I receptors. Activin type II receptors are particularly promiscuous and have been shown to mediate signaling of at least 12 TGF-β ligands including activins, myostatin (GDF8), bone morphogenetic proteins (BMPs) and nodal.

Regulation of Transcriptional Responses via Smads—Based upon genetic studies in *Drosophila* and *Caenorhabditis elegans*, a group of proteins now called Smads have been found to transduce signals from receptor serine kinases and mediate regulation of target gene transcription by activin-A and other TGF-β superfamily members. Structural and functional considerations allow subdivision of Smads into three subfamilies: pathway-specific, common mediator, and inhibitory Smads. Ligand/receptor assembly and activin receptor-like kinase (ALK) phosphorylation triggers a transient ALK/pathway-specific Smad association during which the ALK phosphorylates the Smad on its last two serine residues in the C terminal SSXS motif. Activin-A and TGF-β signals are mediated by the pathway-specific Smads, Smad2 and Smad3, while BMP signals are mediated by Smads 1, 5 and 8. Once activated, pathway-specific Smads form hetero-oligomeric complexes with the common mediator, Smad4. These Smad complexes then translocate into the nucleus and interact directly with DNA and/or with cell-type specific co-activator or co-repressor proteins leading to the activation or repression of target genes. Two vertebrate inhibitory Smads have been identified, Smad 6 and 7, which lack the C-terminal SSXS motif found in the pathway specific Smads. Smad 6 and 7 are inhibitors of Smad signaling and bind to ALKs to prevent phosphorylation and activation of the pathway-specific Smads.

Current methods for antagonizing the activation of TGF-β receptors typically use follistatin or other proteins or agents that compete with the TGF-β receptors for binding, in essence sequestering the ligand away from the receptor. Additional compositions and methods for the use and development of high affinity selective modulators and antagonists of the receptors for TGF-β superfamily of ligands, such as type II activin receptors, are needed.

BRIEF SUMMARY OF THE INVENTION

Embodiments of the invention include variants of the TGF-β superfamily of ligands. In particular, TGF-β variants that fail to produce a ligand/receptor complex, preferably a ligand/receptor complex that is unable to produce a typical intracellular signaling cascade. In one aspect, the ligand may bind to one receptor type and not another. Variants of the invention may include ligands that bind a type II receptor and not a type I receptor, or variants that bind a type I receptor and not a type II receptor. The TGF-β superfamily of ligands includes TGF-βs 1 to 5, the DVR group (e.g., dpp and Vg1), bone morphogenetic proteins (BMPs), myostatin, nodal, activins, inhibins and other members of the superfamily.

Certain embodiments of the invention include an isolated activin-A variant, wherein the activin-A variant is an activin-A antagonist that binds an activin type II receptor but not a type I receptor. In certain aspects the activin-A variant comprises an alteration in the finger region or wrist region of activin-A. The activin-A variant may comprise two or more alterations in the finger region, wrist region or both regions of the activin-A variant. In certain aspects, the activin-A variant is a variant of SEQ ID NO:1 or SEQ ID NO:2. The activin-A variant may comprise a substitution of a non-polar amino acid with a proline, a substitution of a polar amino acid with a proline, a substitution of the wrist region of activin-A with an analogous region from an activin-C, or combinations thereof.

In other embodiments, the activin-A variant is selected from the group consisting of M108A, activin-A/activin-C chimera, S60P, I63P, I105P, M108E, N-terminal deletion or combinations thereof. The activin-A variant may be a M108A activin-A, a M108E activin-A, a S60P activin-A, a I63P activin-A, a I105P activin-A, an activin A/C chimera, and an N-terminal deletion, or various combinations thereof, such as an activin A/C chimera with a M108E substitution. In certain embodiments, the activin-A variant is expressed by a cell comprising an expression vector encoding the activin-A variant.

Further embodiments of the invention include methods of making an activin-A variant comprising obtaining a first cell expressing the activin-A variant, culturing the first cell, and purifying the activin-A variant. In certain embodiments, the cell expressing an activin-A variant is a 293T cell. In a preferred embodiment the activin-A variant is a secreted, mature, dimeric activin-A variant.

In still further embodiments, methods include obtaining at least a second cell expressing an activin type II receptor, type I receptor (such as an ALK4 receptor proteins), or both an activin type II receptor and a type I receptor protein; culturing the second cell, contacting the second cell with the activin-A variant, and assessing complex formation between the activin-A variant and the activin type II receptor, the type I receptor, or both the activin type II receptor and the type I receptor. In certain aspects the cell is a 293T cell. The method may further comprising assessing the ability of the activin type II receptor, the type I receptor or a complex of activin type II receptor and type I receptor to activate cellular signaling pathways. Further embodiments of the invention include assessing activation of cellular signaling pathways comprising assessing transcription from an activin-A activated reporter construct. A reporter construct may be an activin-A agonist activated luciferase reporter construct. In certain aspects the methods include assessing complex formation between the activin-A variant and the activin type II receptor, type I receptor, or both the activin type II receptor and the type I receptor comprises a competitive binding assay. Assessing complex formation between activin-A variant and the activin type II receptor, type I receptor, or both the activin type II receptor and the type I receptor may comprise crosslinking of activin-A variants and the activin type II receptor, type I receptor, or both the activin type II receptor and the type I receptor.

In still further embodiments, methods include modulating signaling in a cell comprising administering to a subject an effective amount of a TGF-β ligand, e.g., an activin-A variant, described herein or a TGF-β ligand variant made by the methods described herein, and inhibiting activin type II receptor/type I receptor complex formation. In certain aspects, the cell is part of a tissue targeted for treatment. In still other aspects the formation of activin/activin type II receptor/type I receptor complex formation is inhibited and/or the inhibition of activin signaling alleviates a pathophysiological condition in the subject. The pathophysiological condition may be selected from the group consisting of reproductive, developmental, skin, metabolic, muscle, bone, hepatic, hematopoietic, central nervous system disorders, gonadal cancer, gastrointestinal cancers, adrenal cancer, and liver dysplasia. In certain embodiments, the administration of activin-A variant promotes liver regeneration in a damaged liver or reduces matrix deposition and keloid formation during wound healing. In still further embodiments, the formation of myostatin/activin type II receptor/type I receptor complex formation is inhibited. In certain aspects, the inhibition of myostatin/activin type II receptor complex formation alleviates a pathophysiological condition. The pathophysiological condition can be muscle, fat, metabolic disorders muscular dystrophy, cancer associated cachexia, AIDS or wasting syndromes. In still further embodiments, the activin-A variant comprises a finger/wrist mutant of activin-A. An activin-A variant may have at least a 50%, 60%, 69%, 95% identity to wild-type activin-A. In certain aspects the activin-A variant may comprise an N-terminal deletion. The formation of an activin-A variant/activin type II receptor complex may be augmented by increasing the expression of the activin-A variant in a cell. The expression of an activin-A variant may be increased by transfecting the cell with an expression construct or expression cassette encoding the activin-A variant. The expression of the activin-A variant may be under the control of constitutive heterologous promoter or under the control of an inducible heterologous promoter.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternative are mutually exclusive, although the disclosure supports a definition that refers to only alternatives and "and/or."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows that mature activin-A protein is present in conditioned medium from 293T cells transfected with Inh βA cDNA as assessed by Western blot using an antibody directed against the mature βA subunit. The protein migrates at ~28 kDa (the βA monomer migrates at ~14 kDa) under non-reducing conditions indicating it is a dimer. FIG. 1B shows the activity of a range of concentrations of activin-A in conditioned medium from 293T cells transfected with Inh βA cDNA as assessed by the induction of the activin-responsive A3-luciferase reporter gene when this reporter is transfected into 293T cells together with the transcription factor FAST2. The effect of 2 nM activin-A on inducing luciferase activity in 293T cells transfected with A3-luciferase and FAST2 is included as a control.

Luciferase activities were normalized relative to β-galactosidase activities and data were presented as fold increases in luciferase activity relative to untreated cells.

Figure 2:
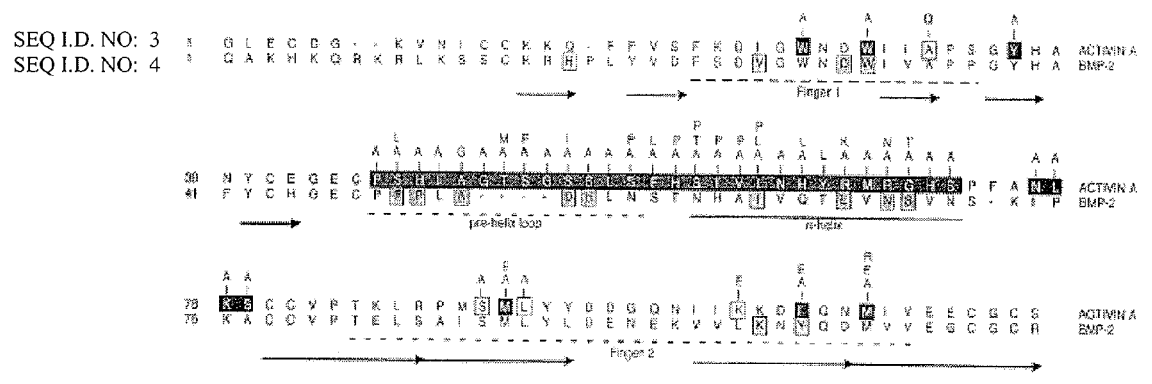

FIG. 2 shows an amino acid alignment of the mature activin-A and BMP2 subunit sequence. Beta sheet sequences are indicated by underline with arrows while β-helices are underlined. BMP2 residues that have previously been identified to be important in type I receptor binding are boxed and shaded grey. Preferred residues mutated individually or combinatorially in the activin-A sequence are shaded black and the residues they have been replaced with are indicated above each residue that was changed.

Figure 3:
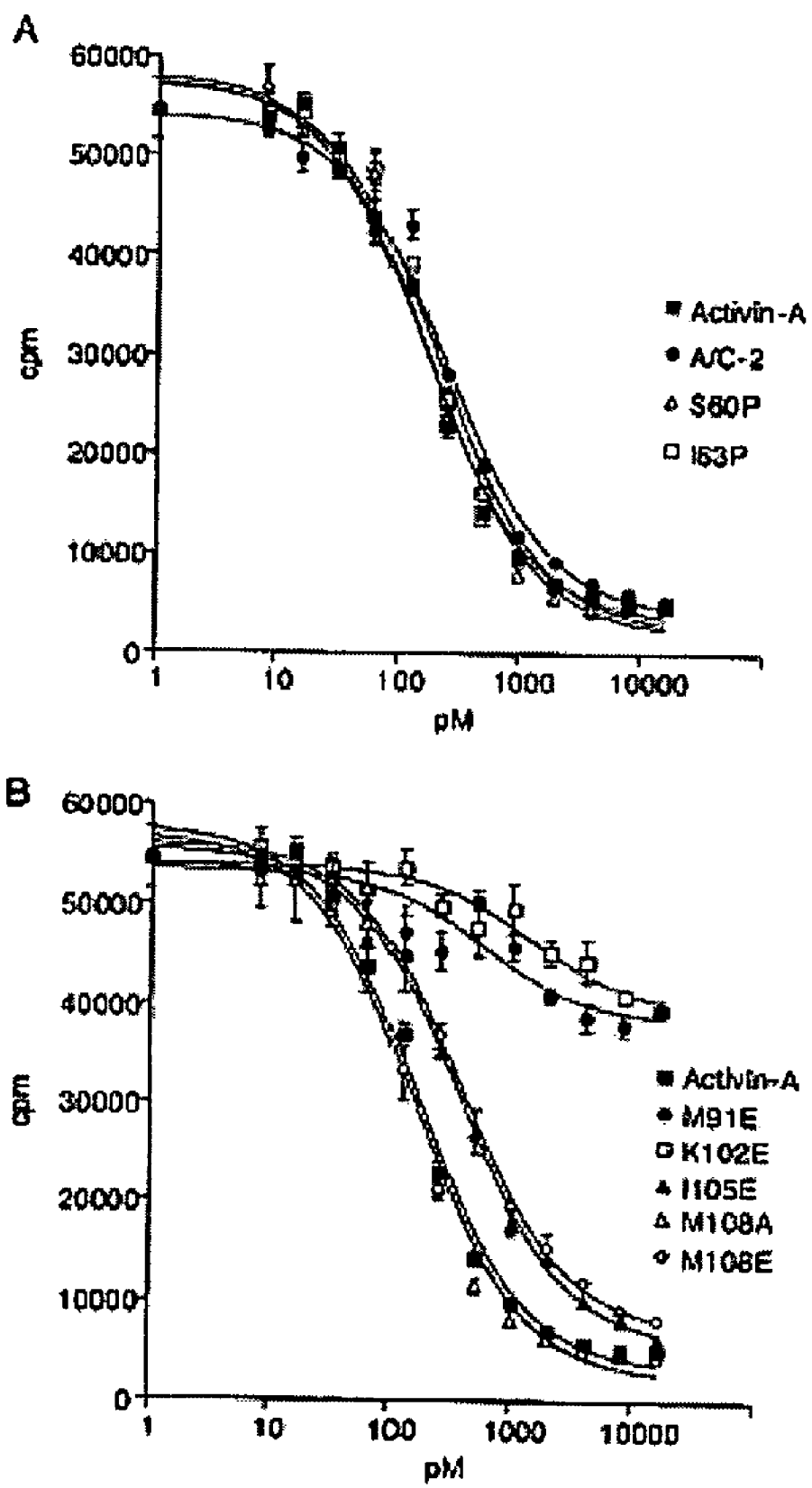

FIGS. 3A and 3B shows competition binding displacement curves for activin-A variants with mutations in the "wrist" region (FIG. 3A) including the A/C 2 mutant (closed circles), S60P (open triangles) and I63P (open squares) mutant and the "finger" region (FIG. 3B) including M91E (open squares), K102E (closed circles), I105E (closed triangles), M108A (open diamonds) and M108E (open triangles) mutants. 293T cells were plated on poly-lysine coated 24 well plates, transfected with ActRII and then treated with 500,000 cpm $^{125}$I-activin-A/well in the presence of the indicated concentration of unlabeled activin-A or activin-A variant. Cells were incubated for 2 h at RT, washed and bound $^{125}$I-activin-A was released in 1% TX-100 buffer and counted using a gamma counter.

FIG. 4 shows dose response curves for wild type activin-A (squares) and the M108A activin mutant (triangles) in 293T cells. 293T cells were transfected with the A3-luciferase and FAST2 constructs and then treated with the indicated doses of wild type activin-A and M108A. Luciferase activities were normalized to β-galactosidase activities and data were presented as fold increase in luciferase activities relative to untreated cells.

FIGS. 5A and 5B show activin-A and M108A binding to non-transfected 293T cells or cells transfected with ActRII and ALK4. Non-transfected 293T cells (FIG. 5A) or cells transfected with ActRII and ALK4 (FIG. 5B) were incubated with $^{125}$I-activin in the presence of increasing doses of unlabelled activin-A (closed squares) or M108A (open triangles). The displacement curves generated were representative of three experiments.

FIG. 6 shows crosslinking of radiolabeled wild type activin-A (FIG. 5A) and radiolabeled M108A (FIG. 5B) to 293T cells transfected with activin receptors. 293T cells were transfected with ActRII-myc, or ActRII-myc and ALK4. Cells were incubated with labeled activin or labeled M108A as indicated, subjected to covalent crosslinking with dissucinylsuberate (DSS), solubilized in lysis buffer, immunoprecipitated using an antibody against myc or ALK4 and then immunoprecipitated proteins were resolved by SDS-PAGE and visualized by autoradiography.

FIGS. 7A-7C shows the effect of M108A on (FIG. 7A) activin-A, (FIG. 7B) myostatin (GDF8) and (FIG. 7C) TGF-β signaling in 293T cells. 293T cells were transfected with A3-luciferase/FAST2 and treated with the indicated concentrations of wildtype activin-A or myostatin or TGF-β in the absence or presence of increasing amounts of M108A. Luciferase values were normalized to β-galactosidase activities and data were presented as fold increase in luciferase activities relative to untreated cells.

FIGS. 8A and 8B show antagonism of activin-A induced FSH secretion from LβT2 cells by the M108A mutant. LβT2 cells were incubated in triplicate with increasing concentrations of activin-A alone or in the presence of different doses of the M108A mutant. Medium was collected after 72 h and FSH was measured by RIA. The values are the mean±SEM from a representative experiment.

FIG. 9 shows ActRII binding. 293T cells transfected with mouse ActRII for 48 h were incubated with $^{125}$I-activin in the presence of increasing concentrations of unlabelled wt activin-A or A/C 46-78 chimera for 2 h. After the incubation cells were washed three times with HDB buffer and lysed with 1% SDS solution. Radioactivity in the lysate was determined using a gamma counter.

FIG. 10 shows bioactivity and antagonism. 293T cells were transfected with the A3 Lux, β-galactosidase and FAST2 constructs for 24 h. To test for activin-A bioactivity cells were then treated with increasing concentration of wt activin-A alone or A/C 46-78 chimera alone for 16-24 hr. To test the A/C 46-78 chimera for activin-A antagonistic properties cells were treated with 100 pM wt activin-A in the presence of increasing concentrations of A/C 46-78 chimera for 16-24 hr. Luciferase activities were normalized to β-galactosidase activities and data are presented as fold induction relative to untreated cells.

FIGS. 11A-11B shows inhibition of FSH release by A/C 46-78. Rat anterior pituitary cells were incubated without (FIG. 11A) or with 160 pM wt activin (FIG. 11B) in the presence of increasing concentrations of the A/C 46-78 chimera. Medium was collected after 72 h, and measured for FSH levels (ng/ml) by RIA.

DESCRIPTION OF ILLUSTRATIVE EMBODIMENTS

Ligands of the TGF-β superfamily, such as activins and other related ligands, signal via membrane associated receptors and control the physiologic behavior of multiple organ systems. Therefore, targeting these receptors with selective modulators or antagonists provides the opportunity for therapeutic intervention in many human diseases. Extensive research has focused on characterizing the molecular and physiologic basis of activin-A action including the identification and characterization of activin receptors, endogenous modulators and antagonists of activin signaling. The physiologic role of activin-A and related molecules has been studied in detail and the results have indicated that several human disorders have the potential to be treated by type II activin receptor modulators and/or antagonists. Embodiments of the invention include compositions and methods for the use and development of high affinity selective modulators and antagonists of receptors for ligands in the TGF-β superfamily, such as type II activin receptors.

All variants described herein and exemplified by variants of activin-A are contemplated in the context of the other TGF-b superfamily members. One of skill in the art would readily recognize and be able to determine the corresponding variants in the various other members of the superfamily. The TGF-β superfamily of ligands includes Bone Morphogenetic Proteins (BMPs) such as BMP-1, BMP-2, BMP-3, BMP-4, BMP-5, BMP-6 and BMP-7, disclosed for instance in U.S. Pat. Nos. 5,108,922, 5,013,649, 5,116,738, 5,106,748, 5,187,076, and 5,141,905; BMP-8 (WO 91/18098); BMP-9 (WO 93/00432); BMP-10 (WO 94/26893); BMP-11 (WO 94/26892); BMP-12 (U.S. Pat. Nos. 5,658,882; and 6,027,919 and WO 95/16035); BMP-15 (WO 96/36710); and BMP-16 (U.S. Pat. No. 5,965,403). Other members of the TGF-β superfamily or variants thereof include the TGF-β proteins like TGF-β1, TGF-β2, TGF-β3, TGF-β4 TGF-β5 (U.S. Pat. Nos. 5,284,763 and 4,886,747; EP0376785); OP1, OP2 and OP3 proteins (U.S. Pat. Nos. 5,011,691 and 5,652,337; WO 91/05802); GDF1 (WO 92/00382); GDF8 (WO 94/21681);

GDF10 (WO 95/10539); GDF1 (WO 96/01845); GDF5 (CDMP1, MP52) (WO 95/04819, WO 96/01316, WO 94/15949, WO 96/14335, WO 93/16099); GDF6 (CDMP2, BMP13) (WO 95/01801, WO 96/14335, WO 95/16035); GDF7 (CDMP3, BMP12) (WO 95/01802 and WO 95/10635); GDF14 (WO 97/36926); GDF15 (WO99/06445); GDF16 (WO99/06556); DPP (Padgett et al., 1987); Vgr-1 (Lyons et al., 1989); Vg-1, (Weeks and Melton, 1987); dorsalin (Basler et al., 1993); MIS (Cate et al., 1986); pCL13 (WO 97/00958); BIP (WO 94/01557), inhibin α, activin βA and activin βB (EP 0222491); activin PC (MP121) (WO 96/01316); activin PE and GDF12 (WO96/02559 and WO98/22492); activin βD (Oda et al., 1995); GDNF (Lin et al., 1993; WO 93/06116); Neurturin (Kotzbauer et al., 1996); Persephin (Milbrandt et al., 1998; WO 97/33911); Artemin (Baloh et al., 1998); Mic-1 (Bootcov et al., 1997); Univin (Stenzel et al., 1994); ADMP (Moos et al., 1995); Nodal (Zhou et al., 1993); and Screw (Arora et al., 1994). All references in this paragraph are each individually incorporated herein by reference in their entirety.

Embodiments of the invention provide compositions and methods for production, identification and antagonism of receptors for the TGF-β superfamily of ligands. Aspects of the invention include methods that use 293T cells for the rapid production and screening of TGF-β ligands, including but not limited to activin-A variants. Variants are screened for properties that include, but are not limited to type II and type I activin receptor binding and functional antagonism of signaling via receptors for the TGF-β superfamily of ligands. The methods in conjunction with competition binding studies are used to identify variants, such as activin-A variants, that bind ActRII with high affinity but have little or no measurable signaling activity and are therefore candidate modulators or antagonists of type II activin receptors. A preferred activin-A variant is the M108A activin-A, which has been shown to be deficient in its ability to form a crosslinked complex with the activin type I receptor, i.e., ALK4, relative to wild type activin. The M108A mutant can antagonize signaling both by wild type activin-A as well as the related ligand myostatin. It is contemplated that M108A and other TGF-β variants identified using the methods described herein, will be capable of antagonizing signaling via TGF-β receptors.

In one embodiment, formation of a TGF-β ligand (for example myostatin)/activin type II receptor complexes may be fully or partially inhibited by activin modulators/antagonists, e.g., M108A or other variants described in the present invention. The TGF-β variants may be introduced directly as purified proteins into the circulation or a target tissue(s). Alternatively, the activin-A variants may be expressed in target tissues using a gene therapy approach. In particular aspects of the invention, the myostatin/activin type II receptor complex formation is inhibited in skeletal muscle and white fat.

In further embodiments, formation of activin/activin type II receptor complexes is fully or partially inhibited by activin modulators/antagonists, including, but not limited to M108A. The activin-A variants may be introduced directly as purified proteins into the circulation or target tissues. Alternatively, activin-A variants may be expressed in target tissues using a gene therapy approach. In certain aspects, activin/activin type II receptor complex formation is inhibited in liver, skin and tumor tissue from multiple sources including, but not limited to breast, pancreas, colon, gonad, adrenal and liver. In addition, antagonism of activin type II receptor signaling may benefit a number of pathophysiological conditions including reproductive, developmental, bone, hematopoietic and central nervous system disorders.

In still a further embodiment, a method for rapidly screening activin mutants in 293T cells in order to identify activin-A variants with partial agonist or antagonist properties for activin type II receptors is contemplated. When the full-length activin-A (Inh βA) cDNA is transfected into 293T cells, the mature, fully active activin-A dimer is secreted into the conditioned medium of the cells. An activin responsive reporter assay has been used in 293T cells to screen for activin mutants capable of partial agonism or antagonism of activin type II receptors. Another embodiment of the current invention involves use of screening methods to identify activin mutants that retain high affinity binding to activin type II receptors, but have defective type I receptor binding as assessed via competition binding and covalent crosslinking studies.

Embodiments of the invention also include transfecting full-length TGF-β1 cDNA into 293T cells, the mature, active TGF-β1 dimer is secreted into the conditioned medium of the cells. A TGF-β responsive reporter assay in 293T cells is used to screen for TGF-β mutants capable of partial agonism or antagonism of TGF-β type II receptors. In certain aspects, the mutation of the methionine residue at position 104 in TGF-β1 to alanine is assessed. This methionine residue is conserved between all members of the TGF-β superfamily and corresponds to methionine 108 in activin, which is involved in type I receptor binding. It is contemplated that mutation of residues in TGF-β superfamily ligands corresponding to methionine 108 in activin-A and methionine 104 in TGF-β1 will generally yield receptor antagonists.

Structural data indicate that activin binds its type II and type I receptors via separate surfaces of the ligand. Activin mutants were sought that: 1) bound type II activin receptors with high affinity; 2) did not bind ALK4; 3) did not activate signaling; and 4) could block or partially block signaling of wild type activin. These activin mutants are predicted to be capable of altering or disrupting signaling via activin type II receptors and may provide useful medical and experimental reagents.

A number of pathophysiological conditions including those involving the musculature, skin, fat, hepatic, gastrointestinal, reproductive, developmental, bone, hematopoietic and central nervous systems may be treated by compositions and methods of the invention. Examples include blockade of myostatin in treating muscular dystrophy and cachexia and blocking activin both in minimizing scarring and facilitating liver regeneration.

III. Antagonism of the TGF-β Superfamily Receptors

Antagonist of various members of the TGF-β superfamily of ligands may be modeled using the structure of BMP2 bound to its type I receptor ALK3. Analysis of the structure of the BMP2/ALK3 complex showed that it made receptor contacts via its wrist region and also via finger residues. Mutagenesis studies with BMP2 confirmed that amino acid residues in these regions play important roles in type I receptor binding. By aligning the amino acid sequence of activin-A with that of BMP2 and identifying the activin-A regions and residues that correspond to those on BMP2 that have been shown to be important for type I receptor binding and function, the inventors have identified similar important type I (i.e., ALK4) binding residues on activin-A. An exemplary alignment is shown in FIG. 2. Residues shown to be important for type I receptor binding by BMP2 are boxed and shaded grey. Activin-A residues that have been shown to be important for type II receptor binding are boxed whereas residues mutated in an exemplary study are shaded black and the residues they were substituted to are shown above each.

A. Activin-A and other TGF-β Polypeptide Variants

Amino acid sequence variants of polypeptides of the invention can be substitutional, insertional or deletion variants. A variant as used herein encompasses mutations, fusions, and chimeric polypeptides that have a detectable alteration in their activity as compared to the activity of a polypeptide with a wildtype activity, which is typically the activity associated with a polypeptide as isolated and/or cloned from an individual with a normal physiology. Deletion variants lack one or more residues of the native protein which are not essential for folding and stability. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as ability to bind one or more component of a receptor complex, without the loss of other functions or properties. Substitutions may or may not be conservative substitution, that is, one amino acid is replaced with another that may or may not be one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create a protein that maintains some functions but lacks others. For example, certain amino acids may be substituted for other amino acids in a protein structure without appreciable loss of interactive binding capacity with one protein such as, for example, binding sites for signal transducing molecules (e.g., a receptor protein kinase). Since it is the interactive capacity and nature of a protein that defines the protein's biological functional activity, certain amino acid substitutions can be made in a protein sequence, and its underlying DNA coding sequence, to obtain a protein with altered properties, such as antagonist properties. It is thus contemplated by the inventors that various changes may be made in the DNA sequences encoding a member of the TGF-β superfamily, e.g., activin-A, without appreciable loss of certain biological activity while lacking another, e.g., ALK 1-7 binding.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, cell surface receptors. It is also understood in the art that the substitution of amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As outlined above, amino acid substitutions are generally based on the character of the amino acid side-chain substituents, for example, their hydrophobicity, hydrophilicity, charge, size, and the like. Exemplary substitutions that take various of the foregoing characteristics into consideration are well known to those of skill in the art. In particular, those that will disrupt one activity of a ligand and not disrupt another, e.g., binding to a type I and type II receptor respectively.

1. Domain Switching

Domain switching involves the generation of chimeric molecules using different polypeptide(s). Chimeric, as used herein, defines a molecule that contains a distinct portion of another molecule, e.g., a chimeric protein may contain a distinct domain or portion of another protein. These molecules may have additional value in that these "chimeras" can be distinguished from natural molecules. For example, the C- or N-terminus of a related family member may provide suitable characteristics for domain switching experiments to alter the ability of an engineered ligand to activate intracellular signaling by a TGF-β superfamily receptor complex, while retaining other properties such as binding to one but not another receptor.

In particular embodiments of the invention, various domains of two ligands of the TGF-β superfamily may be combined to form a chimeric TGF-β ligand. In certain aspects, all or part of the wrist and/or finger regions may combined or switched to form various TGF-β chimeras. For example, 5, 6, 7, 8, 9, 10, 15, 20, 25 or more amino acids, including integers there between, from one or more domain of a first TGF-β superfamily member may replace 5, 6, 7, 8, 9, 10, 15, 20, 25 or more corresponding amino acids of a second TGF-β superfamily member. In a particular embodiment, domains of the activin C and activin A proteins may be switched. For example, amino acids 46 to 78 of activin A may be replaced by the analogous sequences of Activin C. In certain aspects, amino acids 46-53, 54-63, 64-69, or 70-78 of activin A may be substituted by the analogous amino acid sequences of activin C.

2. Fusion Proteins

A specialized kind of insertional variant is the fusion protein. This molecule generally has all or a substantial portion of the native molecule, linked at the N- or C-terminus, to all or a portion of a second polypeptide. For example, fusions may employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as binding sites for receptors or other proteins.

3. Purification of Polypeptides

In certain aspects, it will be desirable to purify activin-A or other TGF-β superfamily variants thereof. Protein purification techniques are well known to those of skill in the art. These techniques involve, at one level, the crude fractionation of a cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a purified polypeptides are ion-exchange chromatography, exclusion chromatography; polyacrylamide gel electrophoresis; and/or isoelectric focusing. A particularly efficient method of purifying peptides is fast protein liquid chromatography or even HPLC. As is generally known in the art, it is believed that the order of conducting the various purification steps may be changed, or that certain steps may be omitted, and still result in a suitable method for the preparation of a substantially purified protein or peptide.

Certain aspects of the present invention concern the expression and purification, and in particular embodiments, the substantial purification, of a member of the TGF-β family of ligands. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of polypeptide will be known to those of skill in the art, in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity. There is no general requirement that the protein or peptide always be provided in their most purified state.

Embodiments of the invention, for example, may comprise methods that include growing 293T cells complete DMEM supplemented with 10% bovine calf serum, penicillin, streptomycin and L-glutamine in 5% $CO_2$ to ~40-60% confluence and transfecting the cells with a cDNA encoding an variant of interest. Approximately 48 h following transfection, conditioned medium is collected and assessed for the presence of the variant polypeptide by either functional assay, by Western blot analysis or a combination thereof.

The conditioned medium from 293T cells transfected with the cDNA of interest typically will contain a mature, dimeric variant polypeptide. The presence of the polypeptide is typically detected by Western blot analysis.

4. Antagonist Screening

Typically, screening for antagonist of a TGF-β superfamily receptor, conditioned medium from a cell (e.g., 293T cell) expressing an variant of a member of the TGF-β superfamily to be assessed, is serially diluted and each fraction is tested for activity using a ligand-responsive luciferase assay. For example, 293T cells are plated on poly-D-lysine-treated 24 well plates at 150,000 cells per well and transfected in triplicate 24 h later with DNA encoding an variant to be screened, a reporter plasmid, and any other supplementary polynucleotides, such as those expressing one or more receptor or transcriptional activator polypeptides. 24 h following transfection the cells are treated with the serially diluted samples and incubated overnight (~16 h). Media is aspirated and cells are solubilized in solubilization buffer (e.g., 1% Triton X-100 solubilization buffer (1% Triton X-100, 25 mM glycylglycine (pH 7.8), 15 mM $MgSO_4$, 4 mM EGTA and 1 mM DTT) and reporter activity is measured and normalized. Conditioned medium from 293T cells transfected with a cDNA encoding an variant of a TGF-β member either induces or inhibits the activation of a promoter controlling the expression of the reporter. The results indicate that the 293T cells transfected with a cDNA of interest secrete functional activin-A or an activin-A antagonist. The Inventors have demonstrated that this assay can be carried out on cells in which Inh βA, FAST2, A3-lux and CMV-β-galactosidase are transfected into the same cells. In this exemplary case, induction of luciferase is the result of activin-A being secreted and then acting back on the cells that secreted it. This provides a rapid indication of the functional status of individual activin-A mutants being assessed. The assessment of an antagonist is conducted by comparing the effect of a candidate antagonist upon the signaling of a wildtype or fully functional ligand. An antagonist will typically compete with and inhibit or antagonize signaling pathways associated with the related receptor.

B. Nucleic Acids Encoding TGF-β Ligands

Embodiments of the invention also provide for nucleic acids encoding various variants or mutants of TGF-β family members, see, Genbank accession number NM_002192. The present invention is not limited in scope to this nucleic acid sequence, however, as one of ordinary skill in the art using the present disclosure as guidance could use these nucleic acids to readily identify and produce various variants of various members of the TGF-β family exemplified herein. In addition, it should be clear that the present invention is not limited to the specific nucleic acids disclosed herein. As discussed below, a "activin-A or TGF-β ligand polynucleotide" may contain a variety of different bases and yet still produce a corresponding polypeptide that is functionally indistinguishable, and in some cases structurally indistinguishable, from the polynucleotide disclosed herein.

Similarly, any reference to a nucleic acid may be read as encompassing a host cell containing that nucleic acid and, in some cases, capable of expressing the product of that nucleic acid. In addition to therapeutic considerations, cells expressing nucleic acids of the present invention may prove useful in the context of screening for agents that repress, inhibit, augment, interfere with, block, abrogate, stimulate or enhance the activity of activin type I, type II, or both type I and type II receptors.

Nucleic acids according to the present invention may encode a variant or chimera of a TGF-β superfamily ligand polynucleotide as set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein.

As used in this application, the term "a nucleic acid or polynucleotide encoding an activin-A or TGF-β superfamily variant" refers to a nucleic acid molecule that has been isolated free of total cellular nucleic acid. In preferred embodiments, the invention concerns a nucleic acid sequence essentially as set forth in NM_002192. The term "as set forth in SEQ ID NO:" means that the nucleic acid sequence substantially corresponds to a portion of NM_002192 or the corresponding nucleic acid or amino acid sequence of a TGF-β superfamily member fererred to herein.

The DNA segments of the present invention include those encoding antagonist of the wildtype TGF-β superfamily ligands.

1. Vectors for Cloning, Gene Transfer and Expression

Within certain embodiments expression vectors are employed to express a TGF-β superfamily polypeptide in a cell, tissue, animal, or subject. In certain embodiments the polypeptide may then be purified. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

a. Regulatory Elements

Throughout this application, the term "expression construct" is meant to include any type of genetic construct containing a nucleic acid coding for a variant of the TGF-β superfamily (e.g., activin-A variant) in which part or all of the nucleic acid encoding sequence is capable of being transcribed. The transcript may be translated into a protein, but it need not be. In certain embodiments, expression includes both transcription of a polynucleotide and translation of mRNA into a gene product. In other embodiments, expression only includes transcription of the nucleic acid encoding a variant of the TGF-β superfamily.

In preferred embodiments, the nucleic acid encoding a variant of the TGF-β superfamily is under transcriptional control of a promoter. A "promoter" refers to a DNA sequence recognized by the synthetic machinery of the cell, or introduced synthetic machinery, required to initiate the specific transcription of a polynucleotide. The phrase "under transcriptional control" means that the promoter is in the correct location and orientation in relation to the nucleic acid (positioned) to control RNA polymerase initiation and expression of the gene. Studies have shown that promoters are composed of discrete functional modules, each consisting of approximately 7-20 bp of DNA, and containing one or more recognition sites for transcriptional activator or repressor proteins.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. Depending on the promoter, it appears that individual elements can function either co-operatively or independently to activate transcription.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

Further, selection of a promoter that is regulated in response to specific physiologic signals can permit inducible expression of the gene product. Several regulatory elements are known that may be employed, in the context of the present invention, to regulate the expression of a polynucleotide. The promoters referred to herein is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. Promoters and enhancers are often overlapping and contiguous, often seeming to have a very similar modular organization. Additionally, other promoter/enhancer combination (for example, as per the Eukaryotic Promoter Data Base EPDB) could also be used to drive expression of a polynucleotide of interest.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

b. Selectable Markers

In certain embodiments of the invention, the cells containing a nucleic acid constructs of the invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

c. Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

2. Delivery of Expression Constructs

There are a number of ways in which expression constructs may be introduced into cells. In certain embodiments of the invention, a vector (also referred to herein as a gene delivery vector) is employed to deliver the expression construct. By way of illustration, in some embodiments, the vector comprises a virus or engineered construct derived from a viral genome. Where viral vectors are employed to deliver a polynucleotide encoding a variant of the TGF-β superfamily, it is generally preferred that they be replication-defective, as is well known to those of skill in the art and as described further herein below.

One of the preferred methods for in vivo delivery of expression constructs involves the use of an adenovirus expression vector. "Adenovirus expression vector" is meant to include those constructs containing adenovirus sequences sufficient to (a) support packaging of the construct and (b) to express a polynucleotide that has been cloned therein. In this context, expression does not require that the gene product be synthesized. In preferred embodiments, the expression vector comprises a genetically engineered form of adenovirus. For exemplary methods and a brief review of adenovirus see Graham et al., 1977; Jones and Shenk, 1978; Graham and Prevec, 1991; Ghosh-Choudhury et al., 1987; Racher et al., 1995, each of which is incorporated by reference.

Alternatively, retroviruses may be used in the delivery of an expression construct to a target cell. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. In order to construct a retroviral vector, a nucleic acid encoding a variant of the TGF-β superfamily is inserted into the viral genome in the place of certain viral sequences to produce a virus that is replication-defective. In order to produce virions, a packaging cell line containing the gag, pol, and env genes but without the LTR and packaging components is constructed (Mann et al., 1983).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of a polynucleotide encoding a variant TGF-β member the expression construct must be delivered into a cell. This delivery may be accomplished in vitro, as in laboratory procedures for transforming cells lines, or in vivo or ex vivo.

Several non-viral gene delivery vectors for the transfer of expression constructs into mammalian cells also are also contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

IV. TGF-β Superfamily Receptors and Interacting Ligands

The ligand binding properties of the TGF-β superfamily receptor extracellular domains (ECDs) have been extensively examined. The crystal structure of the ActRII-ECD was the first to be solved and provided detailed information regarding sites predicted to be involved in receptor:ligand interactions. Subsequent mutational analysis of the ActRII-ECD led to the inventors' identification of a cluster of three hydrophobic amino acid residues on the concave surface of the receptor each of which was required for activin binding and signaling. The importance of these ActRII residues was later confirmed by the crystal structure of the ActRII-ECD bound to BMP7 which showed that the amino acids on ActRII required for activin-A binding make up interfacial contacts between ActRII and BMP7 and are required for BMP7 binding.

The "knuckle" epitope of each finger of each monomer of the BMP7 dimer was shown to fit into the concave surface of each of the two ActRII monomers in the structure. It had previously been shown that mutation of lysine 102 on activin-A disrupted binding to ActRII and this lysine residue corresponds to a finger residue on BMP7 shown by the ActRII-BMP7 structure to be directly in contact with ActRII. An allosteric conformational change was observed in BMP7 in its predicted type I receptor binding site following binding to ActRII. This suggested a general model for cooperative type I/type II receptor assembly induced by BMPs (or activin) to form a hexameric complex containing the dimeric ligand, two type II receptors and two type I receptors.

Advances have also been made in understanding the structural basis of how TGF-β ligands interact with their type I receptors. BMP2 binds its type I receptor (ALK3) in the absence of a type II receptor and this allowed the crystallization of the BMP2-ALK3-ECD complex. This structure showed one BMP2 dimer binds to two type I ECDs via both the "wrist" region and the "finger" region of the ligand and showed that both ligand monomers were involved in contacting each receptor ECD. BMP2 was shown to bind the concave surface of the ALK3-ECDs as had been seen with BMP7 binding to the concave surface of ActRII, but unlike ActRII and BMP7 (or activin), the authors reported a prominent phenylalanine (Phe) protruding from the ALK3-ECD that fit into a hole formed by residues provided by the "finger" of the BMP2 ligand. In addition, several "groove" forming residues on the surface of ALK3 were identified that bound α-helical residues from the "wrist" region of the ligand. Using the crystal structure of BMP2-ALK3 as a guide, the inventors used a mutagenesis and structure/function approach to identify an activin-A binding surface on the type I receptor ALK4-ECD. The ALK4-ECD residues leucine 40 (Leu40), isoleucine 70 (Ile70), valine 73 (Val73), leucine (Leu75) and proline 77 (Pro77) form a contiguous patch on the surface of the ALK4-ECD and were each found to play an important role in the ability of activin to form a crosslinked complex with ALK4 in the presence of ActRII. The ALK3-BMP2 structure indicated a prominent Phe residue on ALK3 that was predicted to be essential for BMP2 binding as well as a groove on the surface of the ALK3 ECD that accommodated the wrist region of BMP2.

The inventors have found that the corresponding Phe residue on ALK4 (Phe85) played a minor role but was not critical for activin binding and mutation of several of the residues on ALK4 that corresponded to groove forming residues on ALK3 had no effect on activin binding. Indeed, although the binding sites overlapped in location they appeared to be dissimilar topographically based on mutational analysis and on structural modeling. Among other differences, this may reflect the fact that unlike BMP2, activin does not bind its type I receptor in the absence of its type II receptor.

A. Regulation of Ligand Access to Receptors

The ways in which individual TGF-β ligands are endogenously regulated prior to their ability to access and activate their respective signaling receptors are complex, tissue-specific and highly variable. Of relevance to the current application, 12 known TGF-β ligands utilize activin type II receptors and of these activins, nodal and myostatin are each regulated differently and provide distinct examples of regulation of ligand access to type II activin receptors. Activins (including activin-A) are secreted in their processed, biologically active form. However, the ability of activins to access and assemble signaling receptors can be inhibited in several distinct ways. Inhibins (α-β) share a β subunit with activins and are TGF-β superfamily members that act in conjunction with the membrane proteoglycan betaglycan to form high affinity complexes with activin type II receptors, thereby preventing these receptors from binding activin-A and initiating signaling. The soluble, extracellular activin binding follistatins bind activins with high-affinity and also block the ability of activin to bind its cell-surface receptors and initiate signaling. In addition, the pseudo (decoy) type I receptor BAMBI (BMP and Activin Membrane-Bound Inhibitor) can bind BMP or activin in nonfunctional complexes with activin-And BMP receptors to block signaling. The inventors have also shown that the nodal co-receptor Cripto can form a complex with activin-A and type II activin receptors and block activin signaling. Nodal is another TGF-β ligand that utilizes type II activin receptors. Unlike activins, however, nodal requires Cripto or a related co-receptor in order to bind type II activin receptors and signal.

Myostatin utilizes a different mechanism in that the myostatin prodomain binds to the cleaved mature myostatin dimer to inhibit its activity. Proteolytic cleavage of the prodomain by a BMP-1/Tolloid-like metalloprotease then releases active myostatin. Myostatin, like activins and to a lesser extent BMPs, can also be bound and inhibited by follistatin. These examples (and notwithstanding additional complex regulation of BMPs that signal via type II activin receptors and have several of their own binding proteins and regulators) illustrate the complexity of cells' abilities to regulate signaling via type II activin receptors in a ligand-specific manner aiding in the developmental, contextual and tissue-specific signaling through these receptors.

V. Activin Type II Receptors as Therapeutic Targets

Activins and related ligands that signal via activin type II receptors control the physiologic behavior of multiple organ systems and, therefore, targeting these receptors with selective modulators or antagonists provides the opportunity for therapeutic intervention in many human diseases. Extensive research has focused on characterizing the molecular and physiologic basis of activin-A action including the identification and characterization of activin receptors and endogenous modulators and antagonists of activin signaling. The physiologic role of activin-A and related molecules has been studied in detail and the results have indicated that several human disorders have the potential to be treated by type II activin receptor modulators and/or antagonists. These include among others: (1) muscular dystrophy, (2) cachexia, (3) wound healing, (4) liver regeneration and (5) cancer. The evidence for type II activin receptor signaling in these processes and the potential benefits of type II activin receptor modulation or antagonism are briefly summarized below.

Muscular Dystrophy. Myostatin is a TGF-β superfamily member that has been well established as a potent negative regulator of skeletal muscle mass. Similar to activin, it has been shown that myostatin binds and signals via ActRII and ActRIIB and that it is inhibited by follistatin. Since it signals via activin type II receptors, it is contemplated that antagonists based on mutant forms of activin with defective ALK4 binding will also antagonize myostatin signaling. Like TGF-β, myostatin binds and is inhibited by its propeptide. There are several potential therapeutic strategies for inhibiting myostatin and include the delivery of purified proteins directly or introducing them by gene therapy approach. Therapeutic candidates for blocking myostatin therefore include follistatin isoforms, the mutant activin-A antagonist(s) as described herein, soluble ActRII/IIB ECDs, inhibin and the myostatin propeptide, possibly in a mutated form to allow binding to myostatin but not proteolytic processing and release. Neutralizing antibodies directed against myostatin have been used experimentally to block myostatin and may also be useful therapeutic reagents. The most direct and potentially important therapeutic application of blocking myostatin activity is the resulting promotion of muscle growth. Importantly, it was recently shown in a mouse model of muscular dystrophy (mdx mice) that blocking myostatin increased muscle size and strength in the dystrophic mice, indicating that agents capable of interrupting myostatin signaling may be beneficial in similarly treating muscular dystrophy in humans.

Cachexia. It has been proposed that myostatin may act as a muscle "chalone," i.e., a circulating hormone that maintains the appropriate size and mass of a particular tissue, in this case skeletal muscle. It has been shown that when introduced artificially, myostatin can cause muscle loss, but also loss of white fat leading to a cachexia-like wasting syndrome with symptoms similar to that seen in cancer and AIDS patients that are highly correlated with morbidity. It was demonstrated in this study that that these symptoms could be attenuated by co-administering inhibitors such as the myostatin prodomain or follistatin with the active myostatin. These results indicate that blockade of myostatin signaling via direct antagonism of type II activin receptors in white fat and skeletal muscle will provide a possible therapeutic tool in treating cachexia.

Wound Repair. Several members of the TGF-β superfamily including activins have been implicated in wound healing and tissue repair processes. Experiments in mice have demonstrated that the level of activin expression in wound tissue is crucial for the repair process. These studies have shown that increased levels of activin correlate with an enhanced healing rate but also with increased scarring. Conversely, decreased levels of activin in wound tissue is associated with slowed wound repair but less scarring in the healed wound. Based on these data, the ability to control and restrict activin levels in wound tissue may facilitate wound healing with reduced scarring. There are several strategies for attenuating activin signaling that include follistatin, soluble ActRII-ECD and an activin receptor antagonist. These reagents could be administered directly to the wound site as purified proteins to prevent excessive matrix deposition seen in keloids, hypertrophic scars and fibrotic disease. Alternatively, these agents could be delivered by a gene therapy approach with skin-specific promoters to limit their expression to skin.

Liver Regeneration. Understanding models and mechanisms of inherent regenerative proliferation of hepatic cells has widespread clinical importance. These include artificially increasing the growth of liver tissue to prevent liver failure that can ensue from hepatitis or liver surgery. It has been shown that activin decreases proliferation of hepatocytes and reversibly reduces liver mass in rodents. The activin inhibitor follistatin has been shown to block these activin effects as has directly decreasing levels of the activin protein itself. Therefore, the inventors contemplate approaches aimed at blocking activin signaling as clinical therapies for promoting liver regeneration. One strategy involves delivery of the follistatin protein into the liver using a gene therapy approach. Alternatively, the ActRII ECD could be introduced in a similar manner with the aim of blocking endogenous activin signaling. As an alternative to gene therapy, these proteins could be also be produced and applied intravenously. In the context of the current application, the inventors contemplate that antagonism of activin type II receptors with a mutant form of activin will be capable of promoting liver growth. Again, such antagonist proteins could be applied directly to the liver tissue or introduced via a gene therapy approach.

Cancer. Both activin-A and TGF-β are tumor suppressors and are well known for their ability to inhibit cellular proliferation in multiple cell types via activation of the Smad2/3 signaling pathway. Importantly, however, despite its antiproliferative effects, Smad2/3 signaling can also exacerbate the cancer phenotype under conditions in which cells have become refractory to Smad2/3-induced growth inhibition. For example, increased production of TGF-β or activin by tumor cells that are no longer growth inhibited by Smad2/3 signals may lead to increased angiogenesis, decreased immune surveillance and/or an increase in the epithelial to mesenchymal transition (EMT) of the tumor cells themselves. Collectively, these effects can lead to increased tumor growth and metastasis. Therefore, while activin-A and TGF-β have antiproliferative effects that can slow the early phase of tumor growth, they also can have tumor promoting activities at later stages and blocking their activities may prove clinically useful in treating more advanced human cancers and in preventing metastasis.

VI. EXAMPLES

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Measurement of Recombinant Activin-A Expressed in and Secreted from 293T Cells 293T cells were grown in complete DMEM supplemented with 10% bovine calf serum, penicillin, streptomycin and L-glutamine in 5% $CO_2$ to ~40-60% confluence and transfected with the human Inh βA cDNA using Perfectin (Gene Therapy Systems) according to the manufacturer's instructions. Approximately 48 h following transfection, conditioned medium was collected and tested for the presence of activin-A both by functional assay and by Western blot analysis (FIG. 1).

Figure 1A:
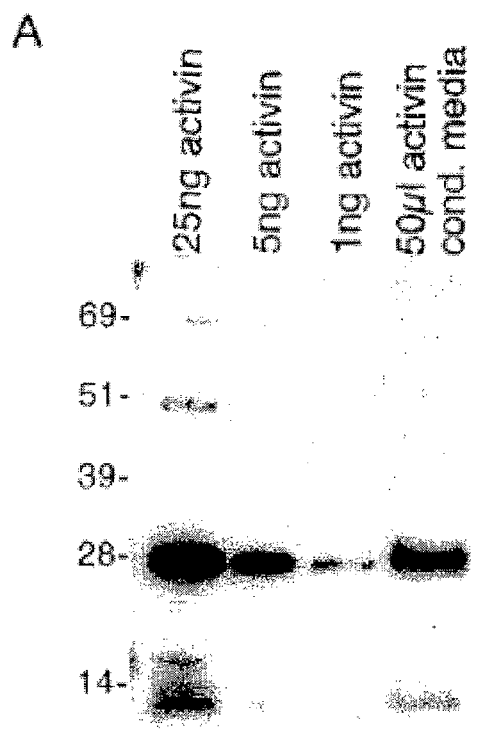
FIGS. 1A and 1B shows that 293T cells transfected with the Inh βA cDNA secrete functional, mature, dimeric activin-A protein into the conditioned medium.

FIG. 1A shows that conditioned medium from 293T cells transfected with Inh βA cDNA contains mature, dimeric activin-A protein as detected by Western blot analysis. SDS-PAGE was carried out under non-reducing conditions on polyacrylamide NuPAGE gels (Invitrogen). Electroblotting to nitrocellulose membranes was carried out in an X-cell II apparatus according to the manufacturer's instructions (Invitrogen). Unbound sites were blocked either 30 min at room temperature or overnight at 4° C. with 5% (w/v) skim milk powder in TBS (50 mM Tris-HCl pH 7.5, 150 mM NaCl). For activin-A detection, blocked membranes were washed three times for 10 min each with TBS containing 0.05% Tween-20 (TBST) and then incubated for 1 h at room temperature with an anti-βA antibody. Membranes were then washed three times for 10 min each with TBST and incubated for 30 min with 2 μg/ml peroxidase-linked anti-rabbit IgG. Blots were washed three times for 10 min each with TBST and reactive bands were visualized using the Pierce Supersignal™ ECL detection system.

Figure 1B:
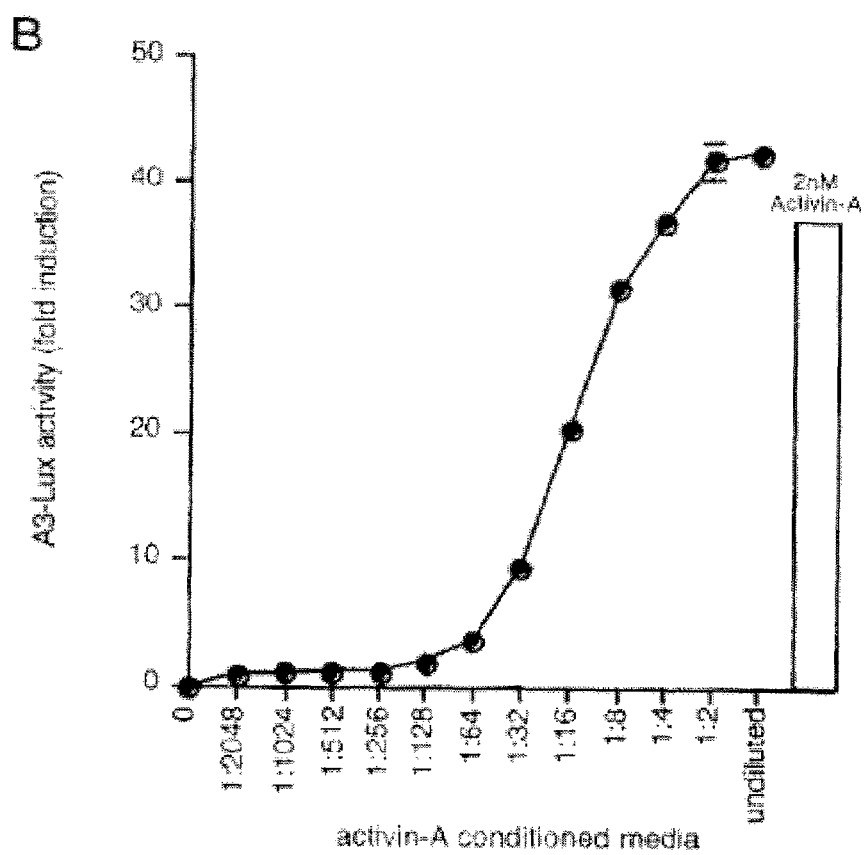

To test for functional activin-A, conditioned medium was serially diluted and each fraction was tested for activity using an activin-responsive luciferase assay. 293T cells were plated on poly-D-lysine-treated 24 well plates at 150,000 cells per well and transfected in triplicate 24 h later with 0.5 μg DNA per well (400 ng pcDNA3.0: 50 ng FAST2: 25 ng A3-lux: 25 ng CMV-βgalactosidase). 24 h following transfection the cells were treated with the serially diluted samples as shown (FIG. 1B) and then incubated overnight (~16 h). Media was aspirated and cells were solubilized in 1% Triton X-100 solubilization buffer (1% Triton X-100, 25 mM glycylglycine (pH 7.8), 15 mM $MgSO_4$, 4 mM EGTA and 1 mM DTT) and luciferase reporter activity was measured and normalized relative to β-galactosidase activities. As shown in FIG. 1B, conditioned medium from 293T cells transfected with the Inh βA cDNA induces the A3-luciferase promoter in a dose-dependent manner. Maximal stimulation of undiluted conditioned medium was comparable to that seen with 2 nM activin-A, a maximal dose (FIG. 1B). These results indicate that 293T cells transfected with the Inh βA cDNA secrete functional activin-A. The inventors have also demonstrated that this assay can be carried out on cells in which Inh βA, FAST2, A3-lux and CMV-β-galactosidase are transfected into the same cells (data not shown). In this case, induction of luciferase is the result of activin-A being secreted and then acting back on the cells that secreted it. This provides a rapid indication of the functional status of individual activin-A mutants being tested.

Example 2

Functional Properties of Activin-A Mutants

To incorporate mutations in the mature region of the full-length Inh βA cDNA, the inventors utilized an overlapping PCR strategy. First, a unique NheI site was introduced just 5' of the mature region in the Inh βA construct allowing the subcloning or mutant PCR products (~600 bp) spanning only the mature region of activin. Primers were constructed to incorporate a 5' NheI site and a 3' XhoI site for subcloning back into the full-length construct. Gel-purified PCR products were digested with NheI and XhoI and then subcloned into NheI/XhoI-digested Inh βA vector. For each construct, the mutated amino terminal mature region was confirmed by DNA sequencing.

As mentioned above, it had previously been shown that BMP2 binds its type I receptor via finger and wrist residues. Therefore, the inventors focused on mutating corresponding residues in these regions of activin-A in efforts to disrupt activin-A binding to ALK4. The inventors primarily made point mutants with alanine substitutions. However, in the wrist region chimeras or other substitutions of multiple residues in the same mutant were made. The functional properties of each of the activin-A mutants listed in Table 1 were determined using the 293T cell luciferase assay described above and were normalized relative to wild type activin-A that was set at 100% activity. As is shown in Table 1, most mutations through the "wrist" region had little effect on activin-A activity. Only substantial mutations, such as exchanging the entire "wrist" region of activin-A for that of the biologically inactive activin-C variant (A/C-2 mutant), or inserting proline residues at certain points with the "wrist" (S60P, I63P), had significant effects on activin-A activity. This is in contrast to the importance of "wrist" residues of BMP2 for binding to ALK3 and highlights important differences in the way activin and BMP2 interact with their type I receptors. Of greater importance for activin binding to ALK4 were residues in "finger 2" of the activin-A ligand. In particular, mutation of residues M91, I105 and M108 had significant effects on activin-A activity (Table 1).

Table 1 contains a summary of functional activity of activin-A variants assessed by methods exemplary of the invention. The amino acid changes are given as well as the epitope of the activin-A molecule within which the changes are made. Finally, for each mutant the activity is given as a % of wild type activin-A activity based on luciferase assays in 293T cells.

TABLE 1

List of mutations introduced into activin A

| Mutant | Epitope | % Activin Activity |
|---|---|---|
| Activin A | | 100 |
| W25A | finger 1 | 73 |
| W28A | finger 1 | ND |
| A31Q | finger 1 | 84 |
| Y35A | finger 1 | 101 |
| P45A/S46A/H47A/I48A | pre-helix | 91 |
| A49G | pre-helix | 82 |
| G50A/T51A | pre-helix | 83 |
| S52A/G53A/S54A | pre-helix | 99 |
| S55A/L56A | pre-helix | 101 |
| S57A | pre-helix | 101 |
| F58A/H59A | pre-helix | 126 |
| S60A/T61A | α-helix | 97 |
| V62A/I63A | α-helix | 83 |
| H65A/M68A | α-helix | 82 |
| R69A/G70A/H71A | α-helix | 82 |
| S72A/P73A/F74A/A75G | α-helix | ND |
| N76A/L77A/K78A/S79A | α-helix | 82 |
| A/C-1 (S46L/T51M/S52P/S54I/S55A/L56A) | pre-helix | 104 |
| A/C-2 (S60T/T61A/I63L/H65L/Y66L/R67K/M68A/R69N/G70T/H71A/S72A) | α-helix | 17 |
| A/C-2.1 (S60T/T61A/I63L) | α-helix | 81 |
| A/C-2.2 (I63L/H65L/Y66L/R67K) | α-helix | 107 |
| A/C-2.3 (Y66L/R67K/M68A/R69N/G70T) | α-helix | 87 |
| A/C-2.4 (M68A/R69N/G70T/H71A/S72A) | α-helix | 79 |
| S57P | pre-helix | 83 |
| H59P | pre-helix | 85 |
| S60P | α-helix | 17 |
| T61P | α-helix | 78 |
| V62P | α-helix | 64 |
| I63P | α-helix | 19 |
| M91A | finger 2 | 74 |
| M91E | finger 2 | 3 |
| I105A | finger 2 | 86 |
| I105E | finger 2 | 13 |
| M108A | finger 2 | 8 |
| M108E | finger 2 | 3 |
| S90A | finger 2 | 59 |
| L92A | finger 2 | 35 |
| K102E | finger 2 | 18 |

A/C-1, chimeric activin A/activin C protein in which amino acids S46-L56 from activin A were replaced by the corresponding residues of activin C (L46-A56).
A/C-2, chimeric activin A/activin C protein in which amino acids S60-S72 from activin A were replaced by the corresponding residues of activin C (T60-A72).
A/C-2.1, 2.2, 2.3, and 2.4 are smaller overlapping versions of the A/C-2 mutant.
ND: Not determined.

Example 3

Competition Binding Studies of Activin-Variants

Activin-A mutants were selected that displayed minimal activity in the functional assay to test whether they retained the ability to bind ActRII. Wrist mutants (FIG. 3A) and finger mutants (FIG. 3B) are shown separately. Binding was performed by first plating 293T cells in poly-D-lysine coated 24 well plates and then transfected using the method described above with 100 ng ActRII. Binding was carried out in the wells at room temperature on intact cells. Cells were washed in HDB and then 200 µl was added to each well: 100 µl binding buffer (HDB with 0.1% BSA, 5 mM $MgSO_4$, 1.5 mM $CaCl_2$), 50 µl unlabeled competitor (activin-A or activin-A mutant as indicated) at various dilutions in binding buffer and 50 µl $^{125}$I-activin-A (500,000 cpm/well). Plates were incubated for 2 h at room temperature and then wells were rinsed in HDB and cells were solubilized in 1% TX-100 and $^{125}$I-activin-A from each was counted using a gamma counter. Binding data were analyzed using the Prism program. As is shown in FIG. 3A, the three activin-A wrist mutants with disrupted activity (A/C-2, S60P, I63P) each retained the ability to bind ActRII, as illustrated by their WT-like ability to displace $^{125}$I-activin-A from 293T cells transfected with ActRII. In contrast, of the five activin "finger" mutants only M108A retained affinity for ActRII comparable to that of WT activin-A (FIG. 3B). M91E, I10SE and M108E were all compromised to varying degrees in their abilities to displace $^{125}$I-activin-A from 293T cells transfected with ActRII (FIG. 3B). The K102E mutant that had previously been shown to have disrupted binding to ActRII was also included as a control in these experiments.

Example 4

The Activin-A (M108A) Variant is Essentially Inactive

The mutant that appeared to have the most favorable properties based on the initial functional screen and the competition binding assay was the M108A variant. This was due its low activity (~8% of wild type) in the functional screen and its high affinity in the competition binding assay (~400 pM). Therefore, this mutant was pursued further as a candidate type II receptor antagonist.

Figure 4:
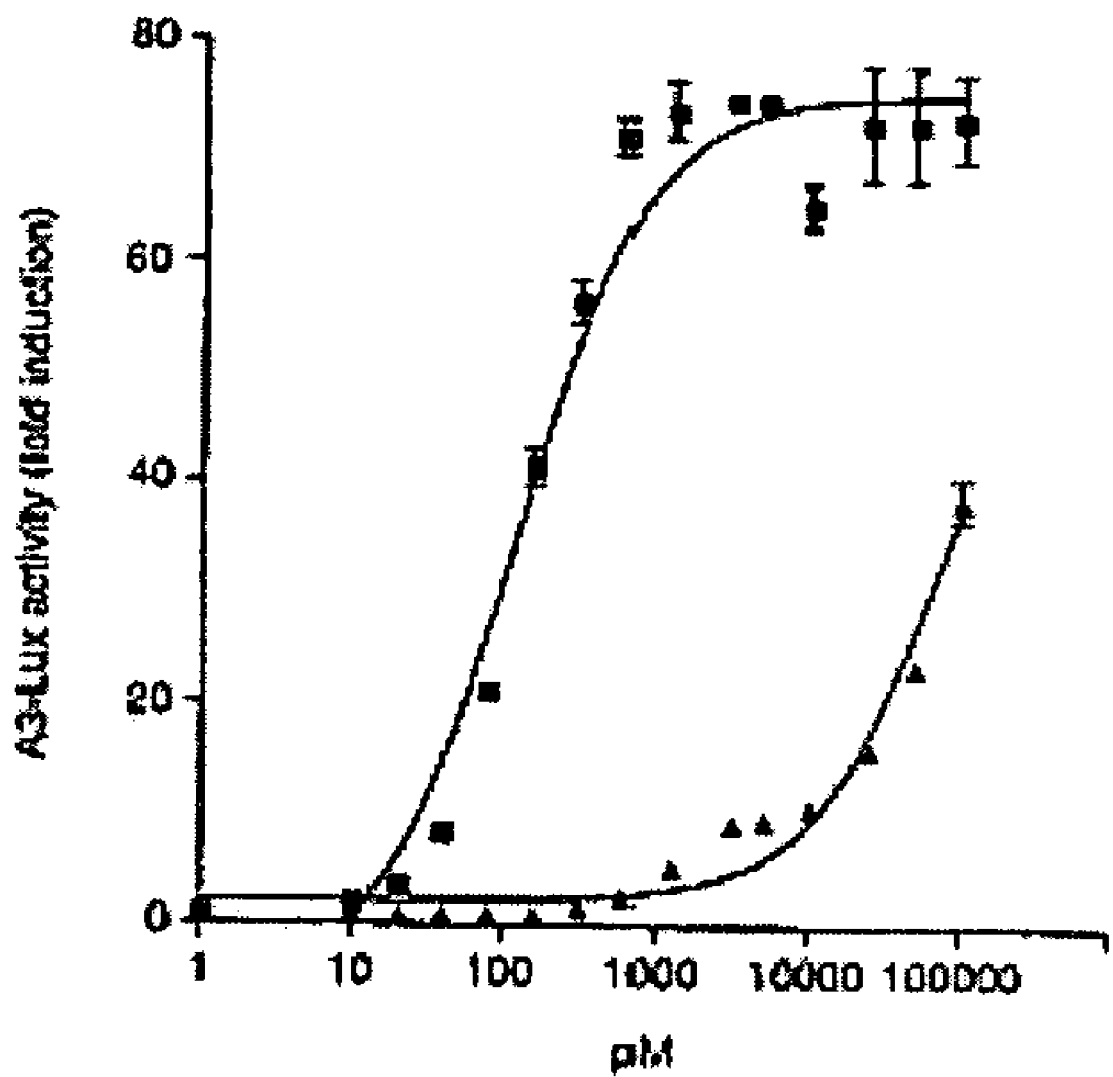
Figure 5:
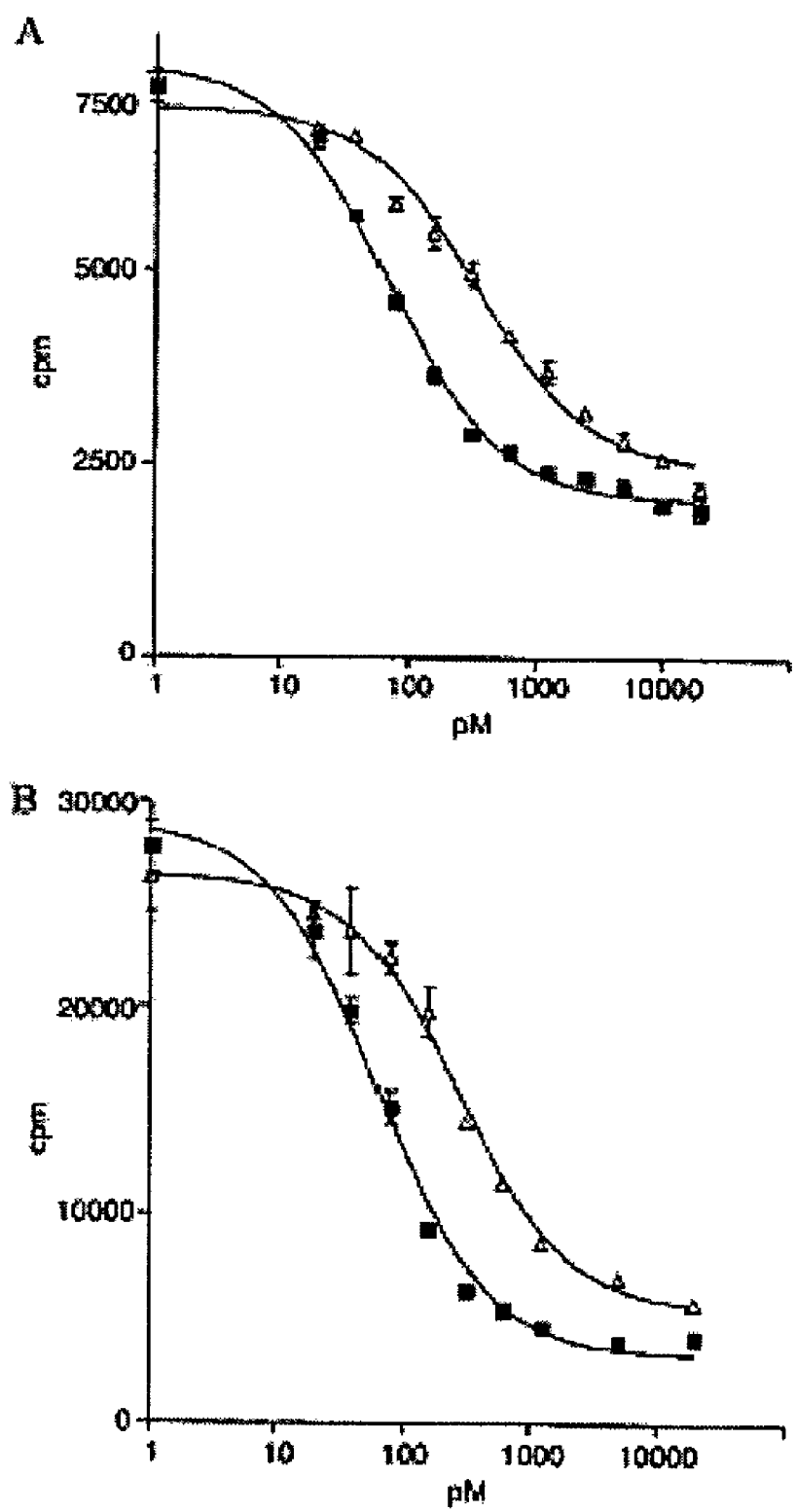
Figure 6:
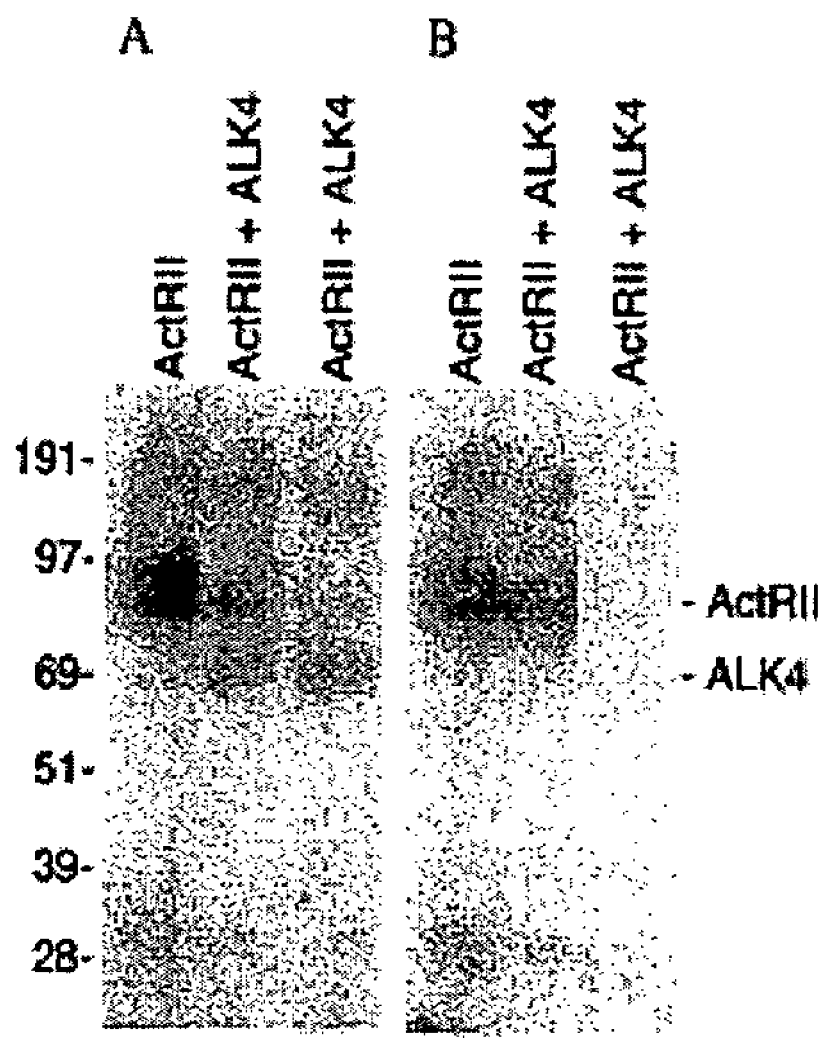

To further characterize the behavior of M108A, luciferase assays were carried out in 293T cells comparing the dose response relationships of wild type activin with that of the M108A mutant. The result is shown in FIG. 4 that illustrates the very low level of activity of the M108A mutant relative to wild type activin-A.

Example 5

Activin and M108A Binding to Non-Transfected 293T Cells or Cells Transfected with ActRII and ALK4

Interestingly, the differences observed in the potencies of wild type activin and the M108A mutant (over 3 orders of magnitude, FIG. 4) were not reflected in their comparable affinities for ActRII (FIG. 3B). To help explain this discrepancy the contribution of ALK4 to activin affinity was examined. In non-transfected 293T cells (FIG. 5A), or cells transfected with both ActRII and ALK4 (FIG. 5B), the apparent affinity of activin was 60-80 pM, or 2-fold higher than the affinity observed in cells transfected with ActRII alone (150 pM). In contrast, the affinity of the M108A mutant for both non-transfected 293T cells (370 pM; FIG. 5A) and cells transfected with ActRII and ALK4 (290 pM; FIG. 5B), was 2-3 fold lower than the affinity observed in cells transfected with ActRII alone (150 pM; FIG. 3B). These results demonstrate for the first time that ALK4 does contribute to the affinity of activin for its receptor complex and suggest that the ability of the M108A mutant to associate with ALK4 is compromised.

Example 6

Crosslinking Studies

M108A binds ActRII with high affinity but has very little signaling activity. Therefore, the mutant would be predicted to be unable to bind the type I receptor ALK4 making it a dominant negative form of activin. To test this directly, μg quantities of M108A was expressed and purified in order to iodinate it and use it in covalent crosslinking studies. To express large quantities of M108A and other activin-A variants, polyethyleneimine (PEI) was used to transfect 293T cells in 15 cm plates and conditioned media was harvested 72 h posttransfection. Activin was purified from conditioned medium using a combination of heparin sepharose chromatography, reversed phase HPLC (C4) and size exclusion chromatography. M108A protein and wild type activin-A were each radioiodinated using the chloramine T method.

For crosslinking, 293T cells were plated on six well plates coated with poly-D-lysine at a density of 400,000 cells per well. Approximately 24 h later, cells were transfected with 2 μg DNA per well with the indicated constructs (the ratio of ActRII:ALK4 was 2:1 and total DNA was kept constant using pcDNA3.0). Cells were incubated an additional 48 h prior to harvesting and then covalent crosslinking was performed by first washing cells in Hepes Dissociation Buffer (HDB) [12.5 mM Hepes (pH 7.4), 140 mM NaCl and 5 mM KCl] and then incubating cells with $^{125}$I-activin-A or $^{125}$I-activin-A (M108A) in binding buffer (HDB containing 0.1% BSA, 5 mM $MgSO_4$ and 1.5 mM $CaCl_2$) at room temperature for 4 h. Cells were washed in HDB, resuspended at 0.5 mM disuccinylsuberate (DSS) in HDB and incubated 30 min on ice. Crosslinking reactions were quenched with TBS (50 mM Tris-HCl pH 7.5, 150 mM NaCl) and cells were solubilized in lysis buffer (TBS containing 1% NP-40, 0.5% deoxycholate and 2 mM EDTA) and subjected to immunopreciptation using anti-myc or anti-ALK4 antibodies as indicated. Immune complexes were analyzed by SDS-PAGE and autoradiography.

FIG. 6A shows that when 293T cells were transfected with ActRII (FIG. 6A, lane 1) and then subjected to labeling and crosslinking with $^{125}$I-activin-A followed by immunoprecipitation with an antibody directed against ActRII, an activin-ActRII crosslinked complex of ~80 kDa was evident consistent with previous crosslinking results. The appearance of two ActRII-activin bands is routinely observed and is likely the result of differential glycosylation of ActRII. Co-transfection of ActRII with ALK4 results in crosslinking of $^{125}$I-activin-A to both receptor types as indicated by the appearance of the activin-ALK4 crosslinked complex at ~60 kDa. The ALK4 band is observed following immunoprecipitation with an antibody against ActRII (FIG. 6A, lane2) or against ALK4 (FIG. 6A, lane 3).

FIG. 6B shows that when 293T cells were transfected with ActRII (FIG. 6B, lane 1) and then subjected to labeling and crosslinking with $^{125}$I-M108A followed by immunoprecipitation with an antibody directed against ActRII, an activin (M108A)-ActRII crosslinked complex of ~80 kDa was evident similar to that seen with wild type labeled activin-A. However, co-transfection of ActRII with ALK4 did not result in crosslinking of $^{125}$I-M108A to both receptor types as the ALK4 band was not visible following immunoprecipitation with antibodies directed against ActRII or ALK4 (FIG. 6B, lanes 2, 3) as had been seen with wild type $^{125}$I-activin-A. These results are consistent with the inability or reduced ability of the M108A mutant to bind ALK4.

Example 7

M108A Antagonizes Activin-A Signaling

The effect of the M108A mutant on activin-A induction of luciferase activity in 293T cells was measured. FIG. 7A shows that cells transfected with A3-luciferase and FAST2 and then treated with 20 nM M108A showed a relatively small (~11 fold) induction that was substantially less than that seen in response to 100 pM activin-A (~48 fold). The addition of increasing amounts of M108A in the presence of a constant dose of WT activin-A (100 pM) caused a significant decrease in the activin-A induced luciferase response (from ~48 fold to ~23 fold). The inhibitory effects are somewhat larger than they appear due to the small intrinsic signaling activity of the M108A mutant.

Example 9

M108A Antagonizes Myostatin Signaling

Figure 7A:
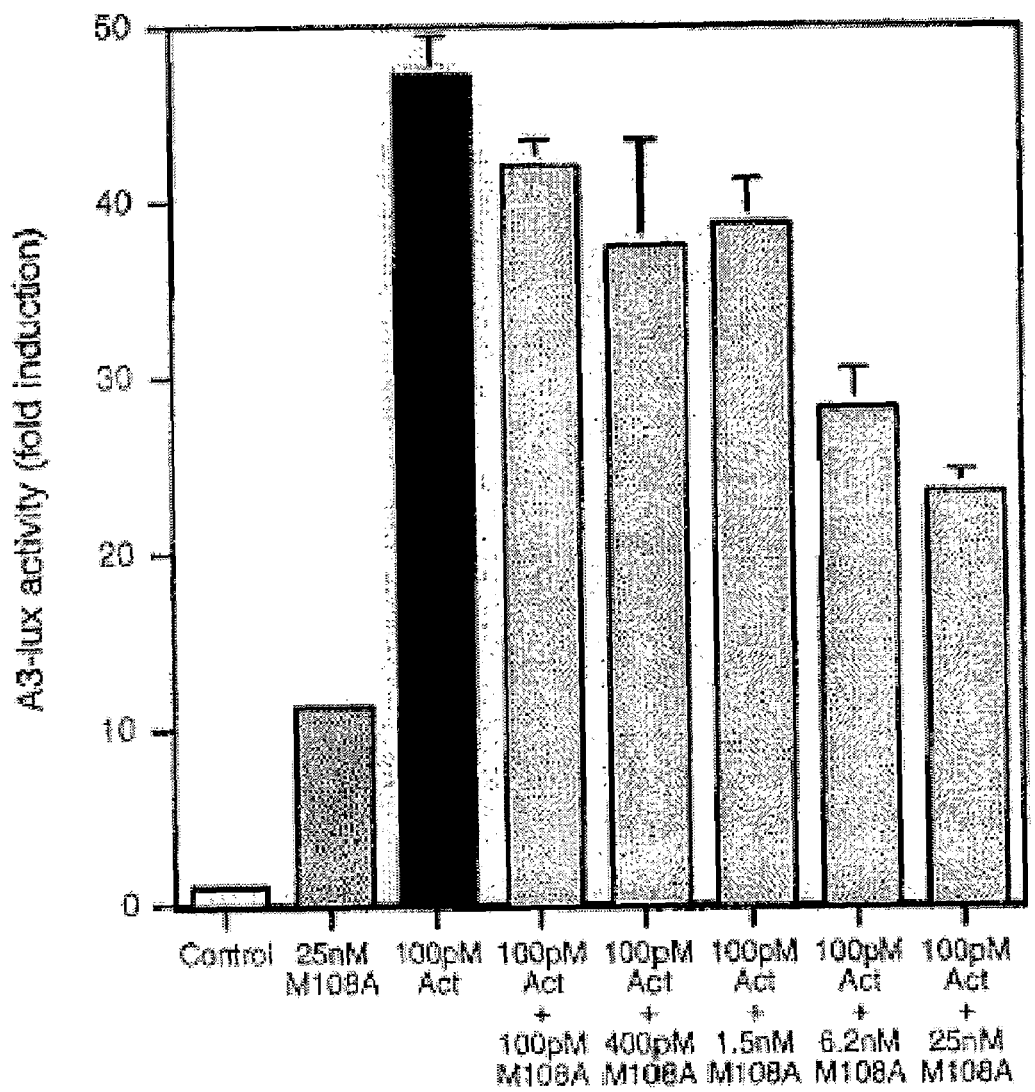
Figure 7B:
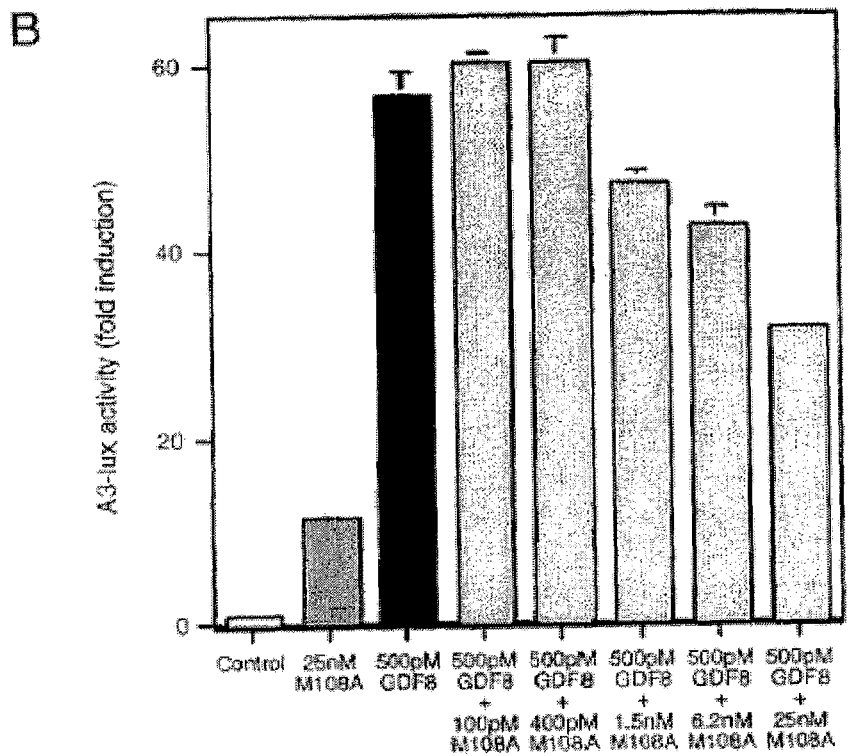

The effect of the M108A mutant on myostatin induction of luciferase activity in 293T cells was also measured. FIG. 7B shows that cells transfected with A3-luciferase and FAST2 and then treated with 20 nM M108A showed a small (~11 fold) induction that was less than that seen in response to 500 pM myostatin (~58 fold). The addition of increasing doses of M108A in the presence of a constant dose of myostatin (500 pM) caused a significant reduction in the myostatin-induced luciferase response (from ~58 fold to ~26 fold). Once again, the inhibitory effects are somewhat larger than they appear due to the small intrinsic signaling activity of the M108A mutant. These data indicate that activin-A (M108A) can block myostatin signaling via type II activin receptors in 293T cells and suggests that this activin-A variant may be generally capable of antagonizing ligands that signal via type II activin receptors.

Example 10

M108A Does Not Antagonize TGF-β Signaling

Figure 7C:
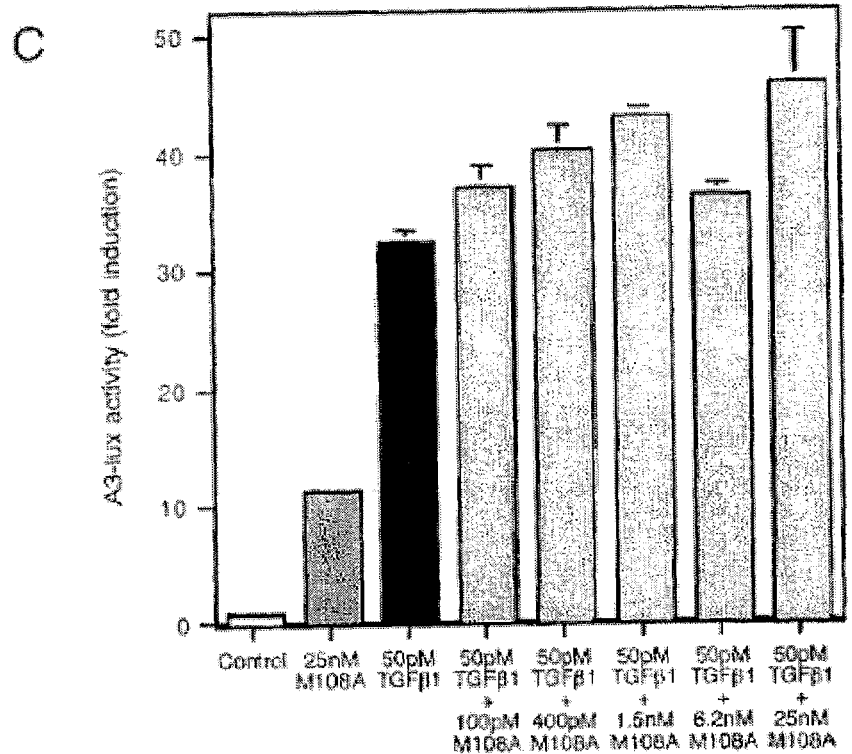

TGF-β does not signal via ActRII/IIB but rather utilizes its own type II receptor (TβRII). Therefore, to demonstrate that M108A specifically antagonizes activin type II receptors, the effect of M108A on TGF-β induction of luciferase activity in 293T cells was determined. FIG. 7C shows that, in contrast to its effects on activin-A and myostatin signaling, addition of increasing doses of M108A to a constant amount of TGF-β (50 pM) led to an apparent increase in TGF-β-induced activity (from 32 fold to 46 fold). This increase most likely reflects the small amount of residual activity observed for M108A (~11 fold). Regardless, this result demonstrates that M108A does not antagonize TGF-β signaling in 293T cells and is consistent with its proposed action as a selective antagonist of type II activin receptors.

Example 11

M108A Blocks Activin-Induced FSH Release from Gondadotrope Cells

Figure 8:
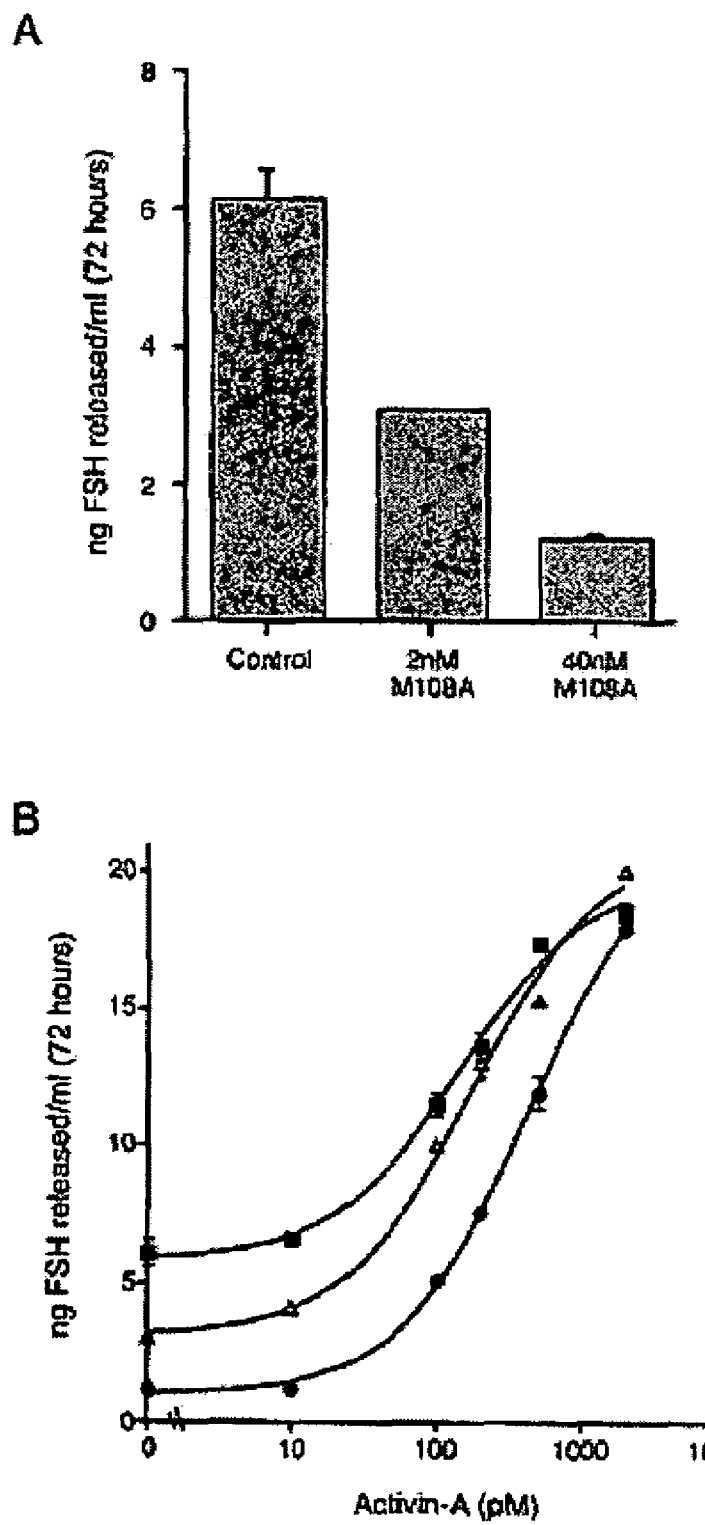
Figure 9:
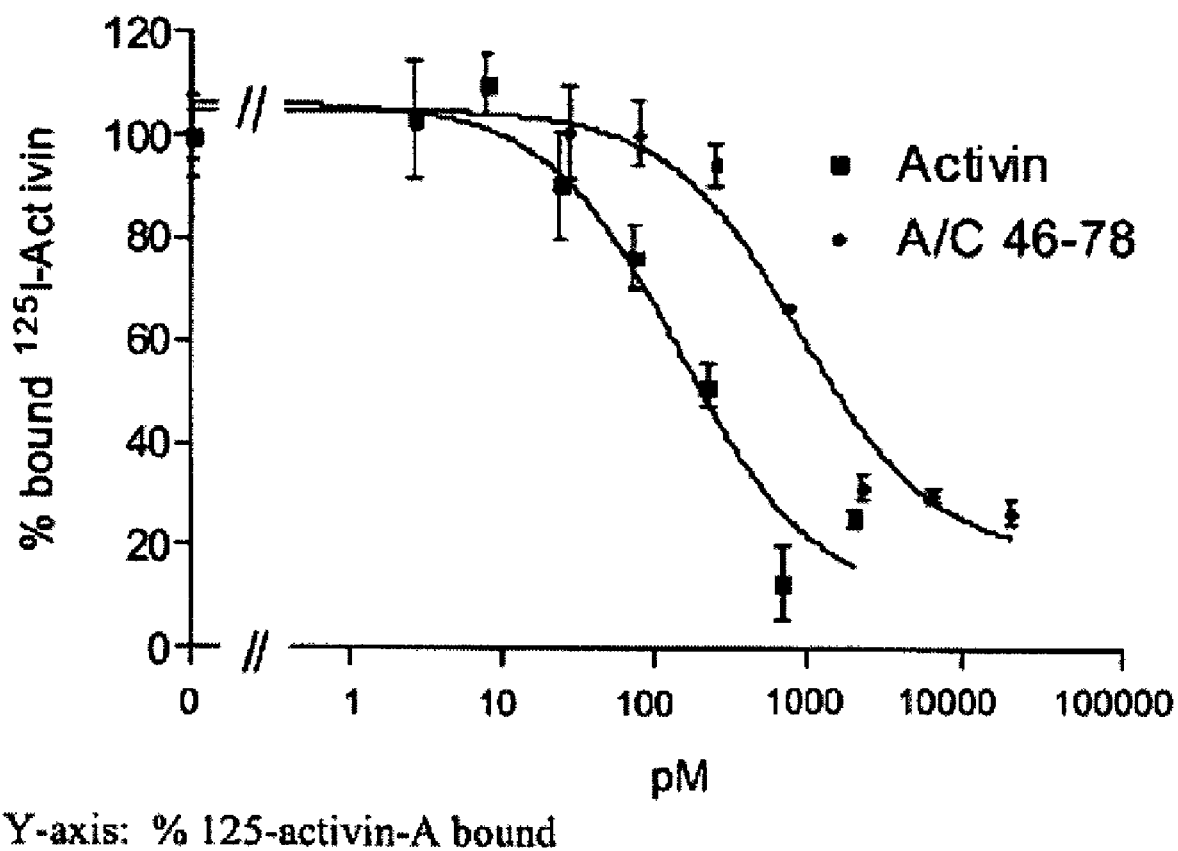
Figure 10:
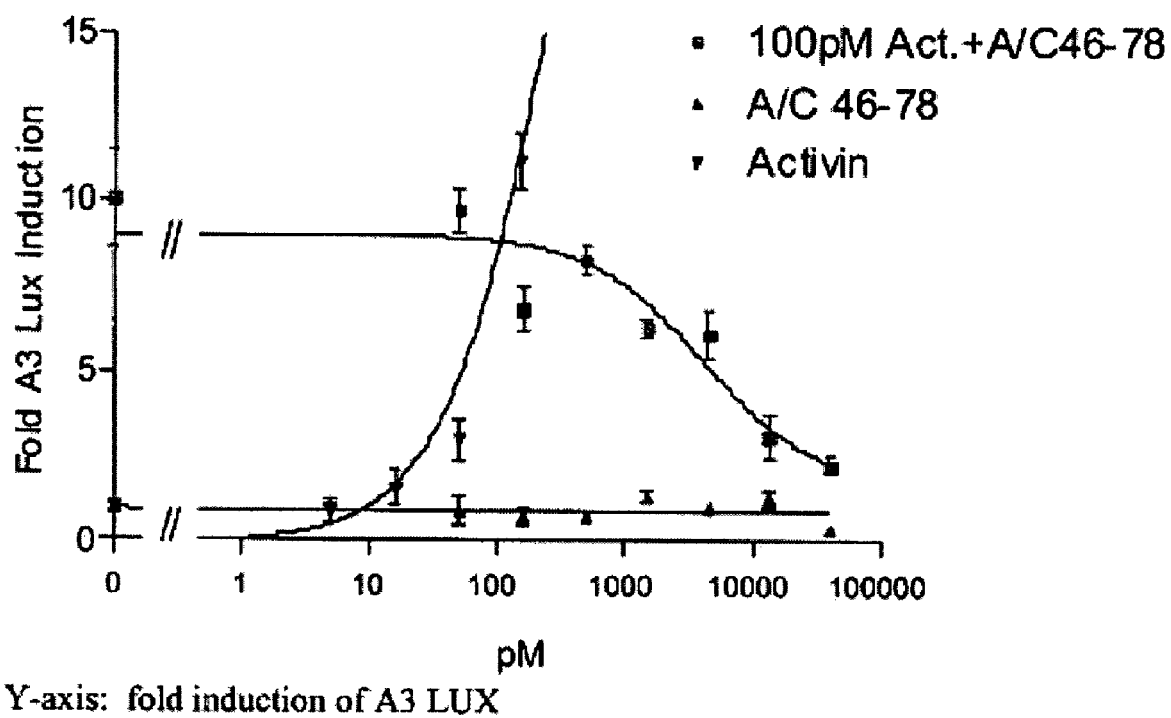
Figure 11A:
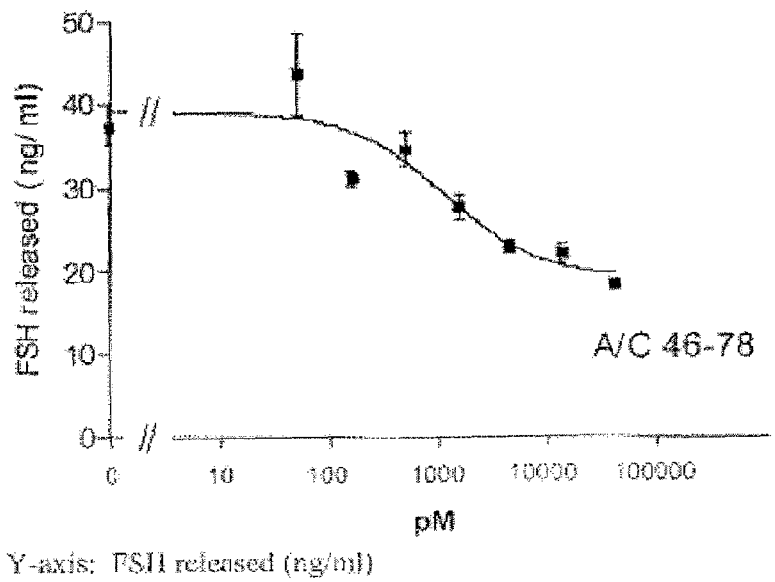
Figure 11B:
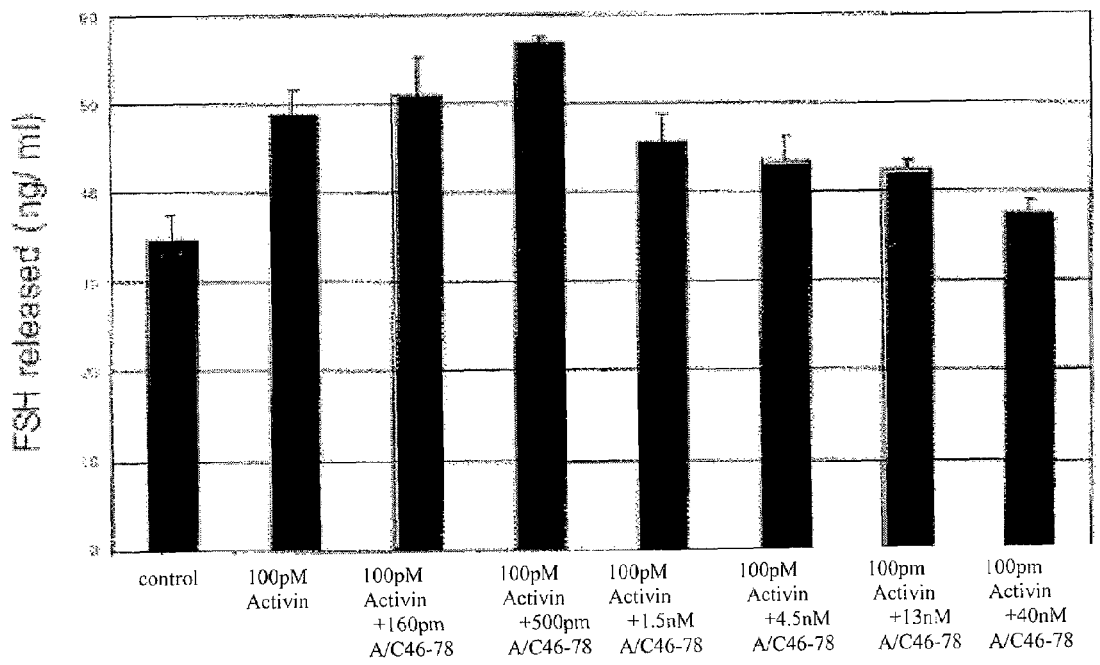

In order to analyze the antagonist activity of the M108A mutant in more detail the inventors determined its ability to block the activin-induced release of FSH from gondadotrope LβT2 cells (FIG. 8). LβT2 cells were plated in 24 well plates at a density of $1.5 \times 10^5$ cells/well. Before initiating experiments, the cells were allowed to recover for 24 h in DMEM supplemented with 2% FBS. The cells were washed three times with the same medium and treated for 72 hours as indicated. FSH was quantified by radioimmunoassay (RIA).

Increasing doses of M108A decreased basal FSH secretion from 17 ng to 6 ng over 72 h, presumably by affecting the action of locally secreted activin. In addition, the M108A mutant attenuated the stimulation of FSH secretion induced by increasing doses of exogenous activin-A (FIG. 8).

Example 12

Activin-A/C Chimera Exhibits Activin-Antagonistic Properties

Activins are involved in many physiologic and pathophysiologic processes and, like other TGF-β superfamily members, signal via type II and type I receptor serine kinases. Ligand residues involved in type II receptor binding are located in the two anti-parallel beta strands of the TGF-β proteins, also known as the fingers. Less is known about ligand residues binding to the type I receptors. The crystal structure of bone morphogenetic protein 2 bound to its type I receptor ALK3, and the activin antagonist M108A-activin implicate residues in the fingers as well as in the wrist loop and helix to bind to the respective type I receptors. Activin-A mutants able to bind ActRII but unable to bind the activin type I receptor ALK4 define ligand residues involved in ALK4 binding and would be potential antagonists.

Therefore, the inventors contemplate engineering a series of activin-A chimeras, such as activin-A/C chimeras, preferably having a peptide tag such a FLAG tag, in each of 8 residues in the wrist loop and helix (such as A/C 46-53, 54-63, 64-69, 70-78) are replaced. Additionally, a chimera was generated in which the entire wrist region (A/C 46-78) was changed from activin-A to activin-C or some other analogous TGF-β member. In one example, the chimeras were assessed for ActRII binding, activin bioactivity as well as antagonistic properties. All five exemplary chimeras retained high affinity for mouse ActRII (EC50: 0.2-0.9 nM, c.f. wild type (wt) activin-A: 0.15 nM). Of these, only A/C 46-78 was devoid of activin bioactivity in an A3 Lux reporter assay in 293T cells at concentrations up to 40 nM. A/C 46-53, 54-63, 64-69 and A/C 70-78 showed activity comparable to wt activin-A (EC50: 0.1-1 nM, c.f. wt activin-A: 0.2 nM). Maximum activity of A/C 64-69 and 70-78, however, was reduced down to about 20-50% and 60-90%, respectively, when compared to wt activin. When tested for activin antagonistic properties in the same assay only the A/C 46-78 chimera showed antagonism (IC50: 4-40 nM). Additionally, A/C 46-78 decreased the basal and activin induced FSH release from cultured rat anterior pituitary cells in a concentration dependent manner. These data indicate that 1) activin residues in the wrist are involved in ALK4 binding and 2) ALK4 binding by residues in the activin wrist involves several weak interactions. The activin antagonist A/C 46-78 may be useful for the study and modulation of activin dependent processes.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,886,747
U.S. Pat. No. 5,011,691
U.S. Pat. No. 5,013,649
U.S. Pat. No. 5,106,748
U.S. Pat. No. 5,108,922
U.S. Pat. No. 5,116,738
U.S. Pat. No. 5,141,905
U.S. Pat. No. 5,187,076
U.S. Pat. No. 5,284,763
U.S. Pat. No. 5,652,337
U.S. Pat. No. 5,658,882
U.S. Pat. No. 5,965,403
U.S. Pat. No. 6,027,919
Arora et al., *Genes Dev.,* 8(21):2588-2601, 1994.
Baichwal and Sugden, In: *Gene Transfer,* Kucherlapati (Ed.), NY, Plenum Press, 117-148, 1986.
Baloh et al., *Neuron.,* 21(6):1291-1302, 1998.
Basler et al., *Cell,* 73(4):687-702, 1993.
Bootcov et al., *Proc. Natl. Acad. Sci. USA,* 94(21):11514-11419, 1997.
Cate et al., Cell 45:685-698, 1986
Chen and Okayama, *Mol. Cell Biol.,* 7(8):2745-2752, 1987.
Coffin, In: *Virology,* Fields et al. (Eds.), Raven Press, NY, 1437-1500, 1990.
Coupar et al., *Gene,* 68:1-10, 1988.
European Appln. 0222491
European Appln. 0376785
Fechheimer, et al., *Proc Natl. Acad. Sci. USA,* 84:8463-8467, 1987.
Fraley et al., *Proc. Natl. Acad. Sci. USA,* 76:3348-3352, 1979.
Friedmann, *Science,* 244:1275-1281, 1989.
Ghosh-Choudhury et al., *EMBO J.,* 6:1733-1739, 1987.
Gopal, *Mol. Cell Biol.,* 5:1188-1190, 1985.
Graham and Prevec, In: *Methods in Molecular Biology: Gene Transfer and Expression Protocol,* Murray (Ed.), Humana Press, Clifton, N.J., 7:109-128, 1991.
Graham and Van Der Eb, *Virology,* 52:456-467, 1973.
Graham et al, *J. General Virology,* 36:59-74, 1977.
Harland and Weintraub, *J. Cell Biol.,* 101(3):1094-1099, 1985.
Hermonat and Muzycska, *Proc. Natl. Acad. Sci. USA,* 81:6466-6470, 1984.
Horwich et al. *J. Virol.,* 64:642-650, 1990.
Jones and Shenk, *Cell,* 13:181-188, 1978.
Kotzbauer et al., *Nature,* 384(6608):467-470, 1996.
Kyte and Doolittle, *J. Mol. Biol.,* 157(1):105-132, 1982.
Lin et al., *Science,* 260(5111):1130-1132, 1993.
Lyons et al., *Proc. Natl. Acad. Sci. USA,* 86(12):4554-4558, 1989
Macejak and Sarnow, *Nature,* 353:90-94, 1991.
Mann et al., *Cell,* 33:153-159, 1983.
Milbrandt et al., *Neuron.,* 20:245-253, 1998.
Moos et al., *Development,* 121(12):4293-4301, 1995.
Nicolau and Sene, *Biochim. Biophys. Acta,* 721:185-190, 1982.
Oda et al., *Biochem. Biophys. Res. Commun.,* 210(2):581-588, 1995.
Padgett et al., Nature. 1987 325(6099):81-4, 1987
PCT Appln. WO 91/05802
PCT Appln. WO 91/18098
PCT Appln. WO 92/00382
PCT Appln. WO 93/00432
PCT Appln. WO 93/06116
PCT Appln. WO 93/16099
PCT Appln. WO 94/01557
PCT Appln. WO 94/15949
PCT Appln. WO 94/21681
PCT Appln. WO 94/26892
PCT Appln. WO 94/26893
PCT Appln. WO 95/01801
PCT Appln. WO 95/01802
PCT Appln. WO 95/04819
PCT Appln. WO 95/10539
PCT Appln. WO 95/10635
PCT Appln. WO 95/16035
PCT Appln. WO 96/01316
PCT Appln. WO 96/01845
PCT Appln. WO 96/14335
PCT Appln. WO 96/36710
PCT Appln. WO 97/00958
PCT Appln. WO 97/33911
PCT Appln. WO 97/36926
PCT Appln. WO 99/06445
PCT Appln. WO 99/06556
PCT Appln. WO96/02559
PCT Appln. WO98/22492
Pelletier and Sonenberg, *Nature,* 334(6180):320-325, 1988.
Potter et al., *Proc. Natl. Acad. Sci. USA,* 81:7161-7165, 1984.
Racher et al., *Biotechnology Techniques,* 9:169-174, 1995.
Ridgeway, In: *Vectors: A survey of molecular cloning vectors and their uses,* Rodriguez and Denhardt (Eds.), Stoneham:Butterworth, 467-492, 1988.
Rippe et al., *Mol. Cell Biol.,* 10:689-695, 1990.
Stenzel et al., *Dev. Biol.,* 166(1):149-158, 1994.
Tur-Kaspa et al., *Mol. Cell Biol.,* 6:716-718, 1986.
Weeks and Melton, *Cell,* 51(5):861-867, 1987.
Wu and Wu, *Biochemistry,* 27:887-892, 1988.
Wu and Wu, *J. Biol. Chem.,* 262:4429-4432,1987.
Yang et al., *Proc. Natl. Acad. Sci. USA,* 87:9568-9572, 1990.
Zhou et al., *Nature,* 361(6412):543-547, 1993.

What is claimed is:

1. An isolated activin-A variant comprising an amino acid variation of the amino acid sequence of SEQ ID NO:3 selected from the group consisting of:
   (i) a M108A substitution,
   (ii) a S60P substitution,
   (iii) a I63P substitution,
   (iv) a I105P substitution,
   (v) a M108E substitution, and
   (vi) a 46-78 activin-A/activin-C chimera.

2. The activin-A variant of claim 1, wherein the activin-A variant comprises two or more amino acid sequence variants selected from the group consisting of a M108A substitution, a S60P substitution, an I63P substitution, an I105P substitution, and a M108E substitution.

3. The activin-A variant of claim 1, wherein the activin-A variant is a 46-78activin-A/activin-C chimera.

4. The activin-A variant of claim 1, wherein the activin-A variant is a M108A activin-A.

5. The activin-A variant of claim 1, wherein the activin-A variant is a M108E activin-A.

6. The activin-A variant of claim 1, wherein the activin-A variant is a S60P activin-A.

7. The activin-A variant of claim 1, wherein the activin-A variant is a I63P activin-A.

8. The activin-A variant of claim 1, wherein the activin-A variant is a I105P activin-A.

* * * * *

UNITED STATES PATENT AND TRADEMARK OFFICE
CERTIFICATE OF CORRECTION

| | | |
|---|---|---|
| PATENT NO. | : 7,575,751 B2 | Page 1 of 1 |
| APPLICATION NO. | : 11/115877 | |
| DATED | : August 18, 2009 | |
| INVENTOR(S) | : Wylie Vale et al. | |

It is certified that error appears in the above-identified patent and that said Letters Patent is hereby corrected as shown below:

In title page, item (75) Inventors, line 3, delete "Encinitas" as the residence of Peter Gray and insert --San Diego-- therefor.

In title page, item (56) References Cited, Foreign Patent Documents, insert
--FR   2 720 069   11/1995
WO   WO-99/06556   2/1999--.

In claim 3, column 34, line 67, insert a space between "46-78" and "activin-A/activin-C".

Signed and Sealed this

Twenty-seventh Day of October, 2009

David J. Kappos
*Director of the United States Patent and Trademark Office*

UNITED STATES PATENT AND TRADEMARK OFFICE
Certificate

Patent No. 7,575,751 B2　　　　　　　　　　　　　　　　　　　　　　Patented: August 18, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Wylie Vale, La Jolla, CA (US); Craig Harrison, Nunawading (AU); Peter Gray, Encinitas, CA (US); Wolfgang Fischer, Encinitas, CA (US); Senyon Choe, Solana Beach, CA (US); and Uwe Muenster, Wuelfrath (DE).

Signed and Sealed this First Day of October 2013.

VANESSA L. FORD
*Supervisory Patent Examiner*
Art Unit 1646
Technology Center 1600

SEQUENCE LISTING

<160> NUMBER OF SEQ ID NOS: 2

<210> SEQ ID NO 1
<211> LENGTH: 1840
<212> TYPE: DNA

<213> ORGANISM: Homo sapiens
<220> FEATURE:
<221> NAME/KEY: CDS
<222> LOCATION: (86)..(1366)

<400> SEQUENCE: 1

```
tccacacaca caaaaaacct gcgcgtgagg ggggaggaaa agcagggcct ttaaaaaggc        60
aatcacaaca acttttgctg ccagg atg ccc ttg ctt tgg ctg aga gga ttt       112
                            Met Pro Leu Leu Trp Leu Arg Gly Phe
                              1               5 ctg ttg gca agt tgc tgg att ata gtg agg agt tcc ccc acc cca gga       160
Leu Leu Ala Ser Cys Trp Ile Ile Val Arg Ser Ser Pro Thr Pro Gly
 10              15                  20                  25 tcc gag ggg cac agc gcg gcc ccc gac tgt ccg tcc tgt gcg ctg gcc       208
Ser Glu Gly His Ser Ala Ala Pro Asp Cys Pro Ser Cys Ala Leu Ala
                 30                  35                  40 gcc ctc cca aag gat gta ccc aac tct cag cca gag atg gtg gag gcc       256
Ala Leu Pro Lys Asp Val Pro Asn Ser Gln Pro Glu Met Val Glu Ala
             45                  50                  55 gtc aag aag cac att tta aac atg ctg cac ttg aag aag aga ccc gat       304
Val Lys Lys His Ile Leu Asn Met Leu His Leu Lys Lys Arg Pro Asp
         60                  65                  70 gtc acc cag ccg gta ccc aag gcg gcg ctt ctg aac gcg atc aga aag       352
Val Thr Gln Pro Val Pro Lys Ala Ala Leu Leu Asn Ala Ile Arg Lys
     75                  80                  85 ctt cat gtg ggc aaa gtc ggg gag aac ggg tat gtg gag ata gag gat       400
Leu His Val Gly Lys Val Gly Glu Asn Gly Tyr Val Glu Ile Glu Asp
 90                  95                 100                 105 gac att gga agg agg gca gaa atg aat gaa ctt atg gag cag acc tcg       448
Asp Ile Gly Arg Arg Ala Glu Met Asn Glu Leu Met Glu Gln Thr Ser
                110                 115                 120 gag atc atc acg ttt gcc gag tca gga aca gcc agg aag acg ctg cac       496
Glu Ile Ile Thr Phe Ala Glu Ser Gly Thr Ala Arg Lys Thr Leu His
            125                 130                 135 ttc gag att tcc aag gaa ggc agt gac ctg tca gtg gtg gag cgt gca       544
Phe Glu Ile Ser Lys Glu Gly Ser Asp Leu Ser Val Val Glu Arg Ala
        140                 145                 150 gaa gtc tgg ctc ttc cta aaa gtc ccc aag gcc aac agg acc agg acc       592
Glu Val Trp Leu Phe Leu Lys Val Pro Lys Ala Asn Arg Thr Arg Thr
    155                 160                 165 aaa gtc acc atc cgc ctc ttc cag cag cag aag cac ccg cag ggc agc       640
Lys Val Thr Ile Arg Leu Phe Gln Gln Gln Lys His Pro Gln Gly Ser
170                 175                 180                 185 ttg gac aca ggg gaa gag gcc gag gaa gtg ggc tta aag ggg gag agg       688
Leu Asp Thr Gly Glu Glu Ala Glu Glu Val Gly Leu Lys Gly Glu Arg
                190                 195                 200 agt gaa ctg ttg ctc tct gaa aaa gta gta gac gct cgg aag agc acc       736
Ser Glu Leu Leu Leu Ser Glu Lys Val Val Asp Ala Arg Lys Ser Thr
            205                 210                 215 tgg cat gtc ttc cct gtc tcc agc agc atc cag cgg ttg ctg gac cag       784
Trp His Val Phe Pro Val Ser Ser Ser Ile Gln Arg Leu Leu Asp Gln
        220                 225                 230 ggc aag agc tcc ctg gac gtt cgg att gcc tgt gag cag tgc cag gag       832
Gly Lys Ser Ser Leu Asp Val Arg Ile Ala Cys Glu Gln Cys Gln Glu
    235                 240                 245 agt ggc gcc agc ttg gtt ctc ctg ggc aag aag aag aaa gaa gag             880
Ser Gly Ala Ser Leu Val Leu Leu Gly Lys Lys Lys Lys Glu Glu
250                 255                 260                 265 gag ggg gaa ggg aaa aag aag ggc gga ggt gaa ggt ggg gca gga gca       928
Glu Gly Glu Gly Lys Lys Lys Gly Gly Gly Glu Gly Gly Ala Gly Ala
```

```
                           270               275                280
gat gag gaa aag gag cag tcg cac aga cct ttc ctc atg ctg cag gcc      976
Asp Glu Glu Lys Glu Gln Ser His Arg Pro Phe Leu Met Leu Gln Ala
                285                 290                 295 cgg cag tct gaa gac cac cct cat cgc cgg cgt cgg cgg ggc ttg gag     1024
Arg Gln Ser Glu Asp His Pro His Arg Arg Arg Arg Arg Gly Leu Glu
            300                 305                 310 tgt gat ggc aag gtc aac atc tgc tgt aag aaa cag ttc ttt gtc agt     1072
Cys Asp Gly Lys Val Asn Ile Cys Cys Lys Lys Gln Phe Phe Val Ser
        315                 320                 325 ttc aag gac atc ggc tgg aat gac tgg atc att gct ccc tct ggc tat     1120
Phe Lys Asp Ile Gly Trp Asn Asp Trp Ile Ile Ala Pro Ser Gly Tyr
330                 335                 340                 345 cat gcc aac tac tgc gag ggt gag tgc ccg agc cat ata gca ggc acg     1168
His Ala Asn Tyr Cys Glu Gly Glu Cys Pro Ser His Ile Ala Gly Thr
                350                 355                 360 tcc ggg tcc tca ctg tcc ttc cac tca aca gtc atc aac cac tac cgc     1216
Ser Gly Ser Ser Leu Ser Phe His Ser Thr Val Ile Asn His Tyr Arg
            365                 370                 375 atg cgg ggc cat agc ccc ttt gcc aac ctc aaa tcg tgc tgt gtg ccc     1264
Met Arg Gly His Ser Pro Phe Ala Asn Leu Lys Ser Cys Cys Val Pro
        380                 385                 390 acc aag ctg aga ccc atg tcc atg ttg tac tat gat gat ggt caa aac     1312
Thr Lys Leu Arg Pro Met Ser Met Leu Tyr Tyr Asp Asp Gly Gln Asn
    395                 400                 405 atc atc aaa aag gac att cag aac atg atc gtg gag gag tgt ggg tgc     1360
Ile Ile Lys Lys Asp Ile Gln Asn Met Ile Val Glu Glu Cys Gly Cys
410                 415                 420                 425 tca tag agttgcccag ccaggggga aagggagcaa gagttgtcca gagaagacag       1416
Ser tggcaaaatg aagaaatttt taaggtttct gagttaacca gaaaaataga aattaaaaac   1476
aaaacaaaac aaaaaaaaaa acaaaaaaaa acaaaagtaa attaaaaaca aacctgatga   1536
aacagatgaa acagatgaag gaagatgtgg aaatcttagc ctgccttagc cagggctcag   1596
agatgaagca gtgaagagac agattgggag ggaaagggag aatggtgtac cctttatttc   1656
ttctgaaatc acactgatga catcagttgt ttaaacgggg tattgtcctt tcccccttg    1716 aggttcccctt gtgagcttga atcaaccaat ctgatctgca gtagtgtgga ctagaacaac  1776
ccaaatagca tctagaaagc catgagtttg aaagggccca tcacaggcac tttcctagcc   1836
taat                                                                1840

<210> SEQ ID NO 2
<211> LENGTH: 426
<212> TYPE: PRT
<213> ORGANISM: Homo sapiens

<400> SEQUENCE: 2

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80
```

-continued

```
Ala Ala Leu Leu Asn Ala Ile Arg Lys Leu His Val Gly Lys Val Gly
            85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
            115                 120                 125

Ser Gly Thr Ala Arg Lys Thr Leu His Phe Glu Ile Ser Lys Glu Gly
            130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
                180                 185                 190

Glu Glu Val Gly Leu Lys Gly Glu Arg Ser Glu Leu Leu Leu Ser Glu
                195                 200                 205

Lys Val Val Asp Ala Arg Lys Ser Thr Trp His Val Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
                260                 265                 270

Gly Gly Gly Glu Gly Gly Ala Gly Ala Asp Glu Glu Lys Glu Gln Ser
                275                 280                 285

His Arg Pro Phe Leu Met Leu Gln Ala Arg Gln Ser Glu Asp His Pro
    290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
                340                 345                 350

Glu Cys Pro Ser His Ile Ala Gly Thr Ser Gly Ser Ser Leu Ser Phe
                355                 360                 365

His Ser Thr Val Ile Asn His Tyr Arg Met Arg Gly His Ser Pro Phe
    370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Cys Gly Cys Ser
                420                 425
```